(12) United States Patent
Satoh et al.

(10) Patent No.: US 6,444,843 B1
(45) Date of Patent: Sep. 3, 2002

(54) PRODUCING METHOD OF (HYDROXYALKYL) ALICYCLIC CARBOXYLIC ACIDS AND INTERMEDIATES FOR PRODUCING THE SAME AND PRODUCING METHOD OF SUCH INTERMEDIATES

(75) Inventors: Yuuichi Satoh, Suita; Jun Tatsumi, Ikoma; Toshiya Iida, Suita, all of (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/541,609

(22) Filed: Apr. 3, 2000

(30) Foreign Application Priority Data

Apr. 7, 1999 (JP) .......................................... 11-100265

(51) Int. Cl.$^7$ ................................................ C07C 67/00
(52) U.S. Cl. ........................ 560/265; 560/254; 562/508
(58) Field of Search ................................ 560/254, 106, 560/265; 562/409, 465, 508

(56) References Cited

U.S. PATENT DOCUMENTS 3,775,472 A * 11/1973 Massie
3,876,688 A * 4/1975 de Raditzky D'Ostrowick et al.
5,189,006 A 2/1993 Augustine et al.

OTHER PUBLICATIONS

Reucil, Journal of the Royal Netherlands Chemical Society 95/2/ pp 45–49 Feb. 1976.*
Organic Chemistry 3$^{rd}$ edition by Morrison and Boyd published by Allyn and Bacon in Boston p. 382 1973.*
CA:106:32081 abs of J Org Chem 51 (22) by Kita et al pp 4150–4158 1986.*
CA: 66:46139 abs of FR 1447136 Jul. 1966.*
CA:120:298187 abs of Synth Commun by Carrijo et al. 24(3) pp 433–440 1994.*

* cited by examiner

Primary Examiner—Jean F. Vollano
(74) Attorney, Agent, or Firm—Staas & Halsey LLP

(57) ABSTRACT

(Acyloxyalkyl)aromatic carboxylic acids are produced by partial oxidation of alkyl substituted aromatic compounds which are represented by the following General Formula (1)

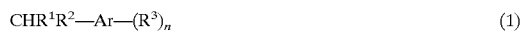

$$CHR^1R^2\text{---}Ar\text{---}(R^3)_n \qquad (1)$$

(where Ar is an aromatic ring of two or greater valency, $R^1$ is a hydrogen atom or alkyl group having a carbon number of 1 to 3, $R^2$ is a hydrogen atom, alkyl group having a carbon number of 1 to 3, or —OCOR$^5$ group, $R^3$ is an alkyl group having a carbon number of 1 to 4, —COOH group, —CHO group, —CH$_2$R$^4$ group, or —COOR group, n is an integer of 1 to 5, $R^4$ is a halogen atom, —OH group, or —OCOR$^5$ group, and $R^5$ is an alkyl group having a carbon number of 1 to 4), and carboxylic acids in the presence of oxygen using a catalyst including an element which belongs to Group VIII of the periodic table. (Hydroxyalkyl)alicyclic carboxylic acids are produced by carrying out hydrogenation and hydrolysis using the (acyloxyalkyl)carboxylic acids as a starting material.

20 Claims, No Drawings

US 6,444,843 B1

PRODUCING METHOD OF (HYDROXYALKYL) ALICYCLIC CARBOXYLIC ACIDS AND INTERMEDIATES FOR PRODUCING THE SAME AND PRODUCING METHOD OF SUCH INTERMEDIATES

FIELD OF THE INVENTION

The present invention relates to producing of bifunctional compounds having two functional groups, which are highly suitable as a raw material for producing a homo-polyester or co-polyester with ethylene glycols, etc. More specifically, the invention relates to a producing method of (hydroxyalkyl)alicyclic carboxylic acids such as (hydroxyalkyl)cyclohexane carboxylic acids, and also relates to intermediates for producing the same and a producing method of such intermediates.

BACKGROUND OF THE INVENTION

In general, bifunctional compounds having two functional groups have their use as a raw material of various synthetic resins and as various chemical agents such as a solvent, or as a raw material of such chemical agents. Particularly, (hydroxyalkyl)alicyclic carboxylic acids, which are one kind of compounds having an alcoholic hydroxy group and a carboxylic group within the same molecule, and of which (hydroxyalkyl)cyclohexane carboxylic acids in particular, are highly useful as a raw material for producing a homo-polyester or co-polyester with ethylene glycols, etc.

For example, French Patent No. 1,447,136 (Published Date: Jun. 20, 1966) discloses a producing method of 4-hydroxymethylcyclohexane carboxylic acid, which is one type of the (hydroxyalkyl)alicyclic carboxylic acids, in which a benzene ring is hydrogenated under the reaction conditions of the reaction temperature of 200° C. and reaction pressure of $1.47 \times 10^7$ Pa, using a p-hydroxymethyl benzoic acid as a reaction substrate and Raney nickel as a catalyst. Also, for example, Japanese Unexamined Patent Publication No. 59188/1997 (Tokukaihei 9-59188) (Published Date: Mar. 4, 1997) discloses a method in which a benzene ring is hydrogenated under the reaction conditions of the reaction temperature of 160° C. and reaction pressure of $4.9 \times 10^6$ Pa, using a terephthalic acid as a reaction substrate and tin-modified Raney ruthenium as a catalyst.

However, there has been no established method of inexpensively and industrially producing the p-hydroxymethyl benzoic acid, which is used as a raw material in the method as disclosed in the above French patent 1,447,136, and the above publication does not disclose such a producing method.

(Hydroxymethyl)aromatic carboxylic acids, such as the p-hydroxymethyl benzoic acid as mentioned above are also one type of compounds having an alcoholic hydroxy group and a carboxylic group within the same molecule, and are a bifunctional compound having two functional groups, which makes these compounds highly useful as a raw material for producing a homo-polyester or co-polyester with ethylene glycol, etc.

For example, U.S. Pat. No. 4,130,719 (Published Date: Dec. 19, 1978) discloses a producing method of a p-hydroxymethyl benzoic acid, in which the side chains of terephthalic acid monoester are reduced using sodium borohydride in an amount above a stoichiometric amount (in excess amount). Also, for example, U.S. Pat. No. 4,448,987 (Published Date: May 15, 1984) discloses a method in which terephthalic acid is subjected to hydrogenation using rhenium oxide as a catalyst. Further, Japanese Unexamined Pat. Publication No. 101334/1975 (Tokukaisho 50-101334) (Published Date: Aug. 11, 1975) discloses a method in which a p-toluic acid used as a staring material is irradiated in the presence of halogen (halogenated) to synthesize a p-halomethyl benzoic acid, followed by hydrolysis. Further, Japanese Unexamined Pat. Publication No. 96541/1973 (Tokukaisho 48-96541) (Published Date: Dec. 10, 1973) discloses a method of obtaining a p-hydroxymethyl benzoic acid, which is generated as a by-product in the synthesis of a terephthalic acid by directly oxidating the side chains of p-xylene.

However, the method as disclosed in the above U.S. Pat. No. 4,130,719 requires an excess amount of reducing agent and the p-hydroxymethyl benzoic acid cannot be produced efficiently and inexpensively. Further, the method as disclosed in the U.S. Pat. No. 4,448,987 requires a reduction process using hydrogen, which in turn requires equipment which can withstand the reaction conditions of high temperature and high pressure, and thus this producing method is not suitable for industrial applications. Furthermore, the method as disclosed in Tokuikaisho 50-101334 requires special equipment which can resist corrosion, etc., in the process of halogenation, and thus this producing system is not suitable either for industrial applications. Further, because the method incorporates halogen and halogenated products, it poses the waste and environmental problems. Also, in the method as disclosed in Tokukaisho 48-96541, the p-hydroxymethyl benzoic acid generated as a by-product is obtained, and thus the method suffers from low productively and constancy, and therefore is not suitable for industrial applications.

That is, all of the conventional producing methods as described above are not suitable for industrial applications, and have the problem that the (hydroxymethyl)aromatic carboxylic acids cannot be produced efficiently and inexpensively. Namely, in the method as disclosed in the French Pat. 1,447,136, it is difficult to obtain the p-hydromethyl benzoic acid as a raw material in industrial applications.

Further, the use of nickel or cobalt such as Raney nickel or Raney cobalt as a catalyst for a hydrogenation reaction as disclosed in the above French Pat. 1,447,136 requires a notoriously high partial pressure of hydrogen in the hydrogenation of the benzene ring, and it also requires a reaction at high temperature, thus requiring special equipment which can withstand this reaction conditions. As a result, the target product 4-hydroxymethyl cyclohexane carboxylic acids cannot be produced inexpensively. Meanwhile, with the use of a catalyst containing palladium or platinum for the hydrogenation of the aromatic ring, the reaction conditions can be relatively relieved, but it still has the problem that the hydroxymethyl group is susceptible to hydrogenolysis, and 4-methylcyclohexane carboxylic acid is easily generated as a by-product, and the selectivity of 4-hydroxymethyl cyclohexane carboxylic acid suffers. Further, in the method as disclosed in the above French Pat. 1,447,136, the catalytic activity of the catalyst used is low, and in order to improve the production efficiency, it requires a large amount of catalyst with respect to the p-hydroxymethyl benzoic acid as a reaction substrate.

Thus, for the reasons described above, the producing method as disclosed in the French Pat. 1,447,136 is not suitable for industrial applications.

Meanwhile, with the method as disclosed in Tokukaihei 9-59188, 4-hydroxymethyl cyclohexane carboxylic acid can be obtained under relatively relieved reaction conditions.

However, in the method as disclosed in Tokukaihei 9-59188, in order to obtain the 4-hydroxymethyl cyclohexane carboxylic acid from the terephthalic acid used as a raw material, it requires hydrogenation of the benzene ring and carbonyl group, and stoichiometrically it requires 5 moles of hydrogen for 1 mole of the raw material. That is, the method of Tokukaihei 9-59188 employs a reaction which consumes a large amount of hydrogen. Further, in this reaction, water is generated as a by-product from the terephthalic acid used as a raw material, which makes the basic unit of the raw material larger. For these reasons, with the method of Tokukaihei 9-59188, the 4-hydroxymethyl cyclohexane carboxylic acid cannot be produced inexpensively.

Furthermore, because the product of the reaction, 4-hydroxymethyl cyclohexane carboxylic acid, and the raw material, terephthalic acid, are hardly soluble in the solvent, to obtain the 4-hydroxymethyl cyclohexane carboxylic acid in high purity, special purifying equipment is required.

Further, producing of tin-modified ruthenium to be used as a catalyst would require special equipment for melting a ruthenium metal and aluminium metal at a high temperature to produce Raney alloy. As a result, the cost of producing the catalyst is increased, which in turn increases the cost of producing the 4-hydroxymethyl cyclohexane carboxylic acid. Thus, this method is not suitable either for industrial applications.

That is, the conventional producing methods as described above are all not suitable for industrial applications, and they all fall short of producing the 4-hydroxymethyl cyclohexane carboxylic acids inexpensively in industrial applications.

Accordingly, there is demand for a method of efficiently and inexpensively producing bifunctional compounds having two functional groups in industrial applications, which are highly useful as a raw material for producing a homo-polyester or co-polyester of ethylene glycols, etc., such bifunctional compounds including (hydroxyalkyl)alicyclic carboxylic acids such as 4-hydroxymethyl cyclohexane carboxylic acids which are one type of (hydroxyalkyl)cyclohexane carboxylic acids, and (hydroxyalkyl)aromatic carboxylic acids such as (hydroxymethyl)aromatic carboxylic acids which are one type of raw materials of the (hydroxyalkyl)alicyclic carboxylic acids.

SUMMARY OF THE INVENTION

The present invention was made to solve the foregoing problems and accordingly it is an object of the present invention to provide in industrial applications a method of efficiently and inexpensively producing (hydroxyalkyl) alicyclic carboxylic acids, such as (hydroxyalkyl) cyclohexane carboxylic acids, which are bifunctional compounds having two functional groups, and which are highly useful as a raw material of a homo-polyester or co-polyester with ethylene glycol, etc., and also their product intermediates.

After extensive research by the inventors of the present application to find a producing method of bifunctional compounds having two functional groups, which are highly useful as a raw material for producing a homo-polyester or co-polyester with ethylene glycols, etc., it was found that (hydroxyalkyl)alicyclic carboxylic acids, which are bifunctional compounds having two functional groups and which are highly useful as a raw material for producing a homo-polyester or co-polyester with ethylene glycols, etc., can be produced both efficiently and inexpensively in industrial applications by carrying out hydrogenation of the aromatic ring and a hydrolysis reaction using (acyloxyalkyl)aromatic carboxylic acids as a raw material, and that the intermediates of such reactions are also bifunctional compounds having two functional groups and are highly useful as a raw material for producing a homo-polyester or co-polyester with ethylene glycols, etc. Further, it was also found that (acyloxyalkyl)aromatic carboxylic acids, which are used as a raw material for producing (hydroxyalkyl)alicyclic carboxylic acids and their product intermediates (precursors), and which are also highly useful as a raw material for producing a homo-polyester or co-polyester with ethylene glycols, etc., can be produced both efficiently and inexpensively in industrial applications by partially oxidizing relatively inexpensive alkyl substituted aromatic compounds, for example, such as xylene, and carboxylic acids such as acetic acid, with are used as a starting material, using a catalyst having a certain composition in the presence of oxygen, thereby accomplishing the present invention.

Namely, in order to achieve the foregoing object, in a producing method of (acyloxyalkyl)aromatic carboxylic acids in accordance with the present invention, the (acyloxyalkyl)aromatic carboxylic acids are produced by partial oxidation of alkyl substituted aromatic compounds which are represented by the following General Formula (1)

$$CHR^1R^2—Ar—(R^3)_n \qquad (1)$$

(where Ar is an aromatic ring of two or greater valency, $R^1$ is a hydrogen atom or alkyl group having a carbon number of 1 to 3, $R^2$ is a hydrogen atom, alkyl group having a carbon number of 1 to 3, or —$OCOR^5$ group, $R^3$ is an alkyl group having a carbon number of 1 to 4, —COOH group, —CHO group, —$CH_2R^4$ group, or —$COOR^5$ group, n is an integer of 1 to 5, $R^4$ is a halogen atom, —OH group, or —$OCOR^5$ group, and $R^5$ is an alkyl group having a carbon number of 1 to 4), and carboxylic acids in the presence of oxygen using a catalyst including an element which belongs to Group VIII of the periodic table.

Further, in order to achieve the foregoing object, the catalyst used to produce the (acyloxyalkyl)aromatic carboxylic acids from the alkyl substituted aromatic compounds as represented by General Formula (1) includes an element which belong to Group VIII of the periodic table. Thus, the (acyloxyalkyl)aromatic carboxylic acids can be produced both efficiently and inexpensively in industrial applications.

Further, in order to achieve the foregoing object, in the producing method of (hydroxyalkyl)aromatic carboxylic acids in accordance with the present invention, (acyloxyalkyl)aromatic carboxylic acids are hydrolyzed. In this case, in order to produce (hydroxyalkyl)aromatic carboxylic acids, and, by extension, (hydroxyalkyl)alicyclic carboxylic acids both efficiently and inexpensively in industrial applications, it is preferable that the (acyloxyalkyl) aromatic carboxylic acids be produced by the described methods. Further, by subjecting the aromatic ring of the (hydroxyalkyl) aromatic carboxylic acids to hydrogenation, the (hydroxyalkyl)alicyclic carboxylic acids can be produced further efficiently and further inexpensively in industrial applications.

Furthermore, by using a catalyst as a reducing catalyst which includes at least one kind of element selected from the group consisting of rhodium and ruthenium in the hydrogenation of the aromatic ring of the (hydroxyalkyl)aromatic carboxylic acids, the (hydroxyalkyl)alicyclic carboxylic acids can be produced efficiently and inexpensively in industrial applications under more relieved conditions as compared with conventional conditions. That is, it is preferable that the catalyst used in hydrogenation of the aromatic ring of the (hydroxyalkyl)aromatic compound group includes at least one kind of element which is selected from the group consisting of rhodium and ruthenium.

Further, in order to achieve the foregoing object, in the producing method of (acyloxyalkyl)alicyclic carboxylic acids in accordance with the present invention, the aromatic ring of the (acyloxyalkyl)aromatic carboxylic acids is subjected to hydrogenation. In this case, in order to produce (acyloxyalkyl)alicyclic carboxylic acids, and, by extension, (hydroxyalkyl)alicyclic carboxylic acids efficiently and inexpensively in industrial applications, it is preferable that the (acyloxyalkyl)aromatic carboxylic acids be produced by the described method. Namely, in order to achieve the foregoing object, the (acyloxyalkyl)alicyclic carboxylic acids in accordance with the present invention is obtained from the hydrogenation of the aromatic ring of the (acyloxyalkyl)aromatic carboxylic acids. The (hydroxyalkyl)alicyclic carboxylic acids can be produced further efficiently and further inexpensively by hydrolyzing (acyloxyalkyl) alicyclic carboxylic acids, or, more preferably, the (acyloxyalkyl)alicyclic carboxylic acids which were obtained by the described method.

Further, in order to achieve the foregoing object, the (acyloxyalkyl)alicyclic carboxylic acids in accordance with the present invention has a structure which is represented by the following General Formula (2)

$$R^6COO—CR^1R^2—Z—COOH \quad (2)$$

(where Z is an alicyclic compound group of two or greater valency, $R^1$ is a hydrogen atom or alkyl group having a carbon number of 1 to 3, $R^2$ is a hydrogen atom, alkyl group having a carbon number of 1 to 3, or —OCOR$^5$ group, $R^5$ is an alkyl group having a carbon number of 1 to 4, and $R^6$ is an alkyl group having a carbon number of 1 to 6, alkenyl group having a carbon number of 1 to 6, alkynyl group having a carbon number of 1 to 6, or a benzene ring, which may or may not include a substituent). Thus, it is possible to efficiently and inexpensively produce in industrial applications the (acyloxyalkyl)alicyclic carboxylic acids, which can be suitably used as precursors (reaction intermediates) of the (hydroxyalkyl)alicyclic carboxylic acids in the production of the (hydroxyalkyl)alicyclic carboxylic acids by hydrolysis.

Other objects, features, and advantages of the present invention will be made clear by the following description. Also, the benefit of the present invention will be clearly understood by the following explanation.

The following will describe the present invention in more detail.

In the method in accordance with the present invention for producing (hydroxyalkyl)alicyclic carboxylic acids, the (hydroxyalkyl)alicyclic carboxylic acids are produced by hydrogenation of the aromatic ring and by hydrolysis, using (acyloxyalkyl)aromatic carboxylic acids as a starting material, and more specifically, the (hydroxyalkyl)alicyclic carboxylic acids are produced from (acyloxyalkyl)aromatic carboxylic acids via (acyloxyalkyl)alicyclic carboxylic acids, or the (hydroxyalkyl)alicyclic carboxylic acids are produced from (acyloxyalkyl)aromatic carboxylic acids via (hydroxyalkyl)aromatic carboxylic acids.

The (acyloxyalkyl)aromatic carboxylic acids used as a raw material in the present invention are not particularly limited as long as they include within the same molecule a group (aromatic ring) of two or greater valency which results from removal of two or more hydrogen atoms from an aromatic ring compound, and a substituent such as acyloxyalkyl group and carboxylic group, and, specifically, the (acyloxyalkyl)aromatic carboxylic acids have a structure which is represented by, for example, the following General Formula (3)

$$R^6COO—CR^1R^2—Ar—COOH \quad (3)$$

(where Ar is an aromatic ring of two or greater valency, $R^1$ is a hydrogen atom or alkyl group having a carbon number of 1 to 3, $R^2$ is a hydrogen atom, alkyl group having a carbon number of 1 to 3, or —OCOR$^5$ group, $R^5$ is an alkyl group having a carbon number of 1 to 4, and $R^6$ is an alkyl group having a carbon number of 1 to 6, alkenyl group having a carbon number of 1 to 6, alkynyl group having a carbon number of 1 to 6, or a benzene ring, which may or may not include a substituent).

More specifically, the aromatic ring of the (acyloxyalkyl) aromatic carboxylic acids indicates a carbocyclic aromatic ring of two or more valency (monocyclic or condensed polycyclic aromatic ring), and a heteroaromatic ring of two or more valency (monocyclic or condensed polycyclic heteroaromatic ring). Further specifically, the aromatic ring of two or more valency indicates, for example, a benzene ring, a condensed ring such as naphthalene ring, or a heterocyclic ring, such as pyridine ring, from which two or more hydrogen atoms have been removed. Also, the (acyloxyalkyl) aromatic carboxylic acids may include a functional group which is inactive toward reactions such as oxidation reaction, hydrogenation, and hydrolysis, which are to be described later.

Specifically, as the (acyloxyalkyl)aromatic carboxylic acids, for example, o-, m-, p-acetoxyalkyl benzoic acids, such as o-, m-, p-acetoxymethyl benzoic acids are available but are not particularly limited to these.

The (acyloxyalkyl)aromatic carboxylic acids can be obtained efficiently and inexpensively in industrial applications by partially oxidizing (oxidative esterification reaction) the alkyl substituted aromatic compounds, which are represented, for example, by the following General Formula (1)

$$CHR^1R^2—Ar—(R^3)_n \quad (1)$$

(where Ar is an aromatic ring of two or greater valency, $R^1$ is a hydrogen atom or alkyl group having a carbon number of 1 to 3, $R^2$ is a hydrogen atom, or alkyl group having a carbon number of 1 to 3, or —OCOR$^5$, $R^3$ is an alkyl group having a carbon number of 1 to 4, —COOH group, —CHO group, —CH$_2$R$^4$ group, or —COOR$^5$ group, n is an integer of 1 to 5, $R^4$ is a halogen atom, or —OH group, or —OCOR$^5$ group, and $R^5$ is an alkyl group having a carbon number of 1 to 4), and carboxylic acids in the presence of oxygen, using a catalyst including an element which belongs to Group VIII of the periodic table. That is, in the (acyloxyalkyl) aromatic carboxylic acids as represented by General Formula (3), the substituent R$^6$CO— derives, for example, from carboxylic acids.

The aromatic ring of two or greater valency as represented by Ar in General Formula (1) indicates a group of two or greater valency in which two or more hydrogen atoms have been removed from the aromatic compound, and more specifically, it indicates a carbocyclic aromatic ring of two or greater valency (monocyclic or condensed polycyclic aromatic ring), and a heteroaromatic ring of two or greater valency (monocyclic or condensed polycyclic heteroaromatic ring). Further specifically, the aromatic ring of two or greater valency indicates, for example, a benzene ring, a condensed ring such as naphthalene ring, or a heterocyclic ring, such as pyridine ring, from which two or more hydrogen atoms have been removed.

The alkyl substituted aromatic compounds are not particularly limited as long as they include within the same molecule a substituent, such as an alkyl group, which can be oxidized partially. Further, the alkyl substituted aromatic compounds may include a functional group which is inactive toward the oxidation reaction of the present invention.

Specifically, as the alkyl substituted aromatic compounds, for example, the following compounds are available: o-, m-, p-alkyl substituted toluenes such as xylene, ethyl toluene, n-propyl toluene, isopropyl toluene, and butyl toluene; o-, m-, p-dialkyl substituted benzenes such as diethyl benzene; o-, m-, p-alkyl substituted hydroxymethyl toluenes such as hydroxymethyl toluene and (hydroxymethyl)ethyl benzene; o-, m-, p-alkyl substituted benzoaldehydes such as methylbenzaldehyde and ethylbenzaldehyde; o-, m-, p-alkyl substituted benzoic acids such as methyl benzoic acid and ethyl benzoic acid; o-, m-, p-alkyl substituted benzoic acid esters such as methyl benzoic acid methyl ester and ethyl benzoic acid methyl ester; o-, m-, p-carboxyalkyl substituted toluenes such as methyl benzyl acetate; o-, m-, p-di (carboxylalkyl) substituted benzenes such as xylylene diacetate; dialkyl substituted naphthalenes such as dimethylnaphthalene; alkyl substituted naphthalene carboxylic acids such as methyl naphtoic acid; and dialkyl substituted pyridines such as dimethyl pyridine (lutidine). of these alkyl substituted aromatic compounds as exemplified above, o-, m-, p-xylene, o-, m-, p-hydroxymethyl toluene, o-, m-, p-methylbenzoaldehyde, o-, m-, p-methyl benzoic acid, o-, m-, p-methyl benzyl acetate, and o-, m-, p-xylylene diacetate are more preferable.

As the carboxylic acids used as a raw material in the producing method of the (acyloxyalkyl)aromatic carboxylic acids, monocarboxylic acids are preferable, and, specifically, for example, the following compounds but not limited to these are available: aliphatic carboxylic acids such as acetic acid, propionic acid, butanoic acid, acrylic acid, and mathacrylic acid; and aromatic carboxylic acids such as benzoic acid. Of these carboxylic acids as exemplified above, acetic acid is more preferable.

The mole ratio of the carboxylic acids with respect to the alkyl substituted aromatic compounds is not particularly limited, but a range of 1:1 to 20:1 is more preferable. When the mole ratio is below 1:1, the carboxylic acids will be deficient, and the (acyloxyalkyl)aromatic carboxylic acids may not be produced efficiently. On the other hand, even when the carboxylic acids are used at a mole ratio which exceeds 20:1, a significant improvement in yield, etc., cannot be expected as compared with the mole ratio in the above range. In fact, in such a case, since the carboxylic acids are used in a large amount, it might increase the size of the reaction apparatus and the recovering device for recovering the excess carboxylic acids, thus possibly increasing the production cost, including the recovering cost.

The catalyst (oxidation reaction catalyst) used in the producing method of the (acyloxyalkyl)aromatic carboxylic acids includes an element which belongs to Group VIII of the periodic table ("Group VIII element" hereinafter).

Specifically, as the Group VIII element, nickel, palladium, platinum, and rhodium are available. These Group VIII elements may be used individually or in combination of two or more kinds. Also, of these Group VIII elements, palladium is particularly preferable.

When the Group VIII element is, for example, palladium, the catalyst may be a palladium such as metal palladium, palladium black, and palladium oxide, or the catalyst may be a supported catalyst immobilizing a palladium compound on a support.

Specifically, as such a palladium compound, for example, the following compounds but not particularly limited to these are available: palladium nitrate, palladium sulfate, palladium acetate, ammonium hexachloro palladate, sodium hexachloro palladate, potassium hexachloro palladate, ammonium tetrachloro palladate, sodium tetrachloro palladate, potassium tetrachloro palladate, potassium tetrabromo palladate, potassium tetracyano palladate, palladium chloride, palladium bromide, palladium iodide, chlorocarbonyl palladium, potassium dinitrosulfite palladate, dinitrodiamine palladium, potassium dinitrosulfite palladate, dinitrodiamine palladium, tetraammine palladium chloride, tetraammine palladium nitrate, cis-dichlorodiamine palladium, trans-dichlorodiamine palladium, bistriphenyl phosphone palladium dichloride, dichloro (ethylenediamine) palladium. Also, the palladium compound may be a supported catalyst immobilizing metal palladium or palladium oxide on a support. These palladium compounds may be used individually or in combination of two or more kinds. Also, of these palladium compounds as exemplified above, palladium nitrate, palladium sulfate, palladium acetate, ammonium hexachloro palladate, palladium chloride, and tetraammine palladium chloride are more preferable.

Further, for example, for the purpose of further improving the catalytic activity or preventing elution of the Group VIII element into the reaction liquid during reaction, in addition to the Group VIII element, the catalyst may further include as required at least one type of element ("second element group" hereinafter) which is selected from the group consisting of Group IB, Group IIB, Group III, Group IV, Group V, Group VI, and Group VIIA of the periodic table. Specifically, as such a second element group, copper, silver, gold, zinc, cadmium, mercury, thallium, tin, bismuth, arsenic, antimony, and terullium, etc., are available. These second element group may be used individually or in combination of two or more kinds of these second element group, gold is particularly preferable.

Further, for example, for the purpose of further improving the catalytic activity, in addition to the Group VIII element, the catalyst may further include as required at least one type of element ("third element group" hereinafter) which is selected from the group consisting of alkali metal and alkali earth metal. Specifically, as such a third element group, for example, potassium acetate, secium acetate, and barium acetate, etc., are available but not particularly limited to these. These third element group may be used individually or in combination of two or more kinds.

That is, in addition to the Group VIII element, the catalyst may further include second element group and/or third element group as required. When the catalyst is to include these groups, the Group VIII element, second element group, and/or third element group may exist as a mixture of, for example, a compound including the Group VIII element, a compound including a second element group, and/or a compound including a third element group, or, alternatively, as a compound (composite) including the Group VIII element and, as components of the composite, second element group and/or third element group, or, further alternatively, as a combination of these combined states.

When the catalyst is a supported catalyst immobilizing the Group VIII element (and second element group and/or third element group) on a support, inorganic compounds but not limited these are suitably adopted as the support, and porous inorganic compounds are most preferable. Specifically, as the support, for example, the following compounds but not particularly limited to these are available: isocrystalline or amorphous metal oxides or composite oxides, such as silicon oxide (silica), aluminium oxide (alumina), titanium oxide (titania), zirconium oxide (zirconia), magnesium oxide (magnesia), silica•alumina, silica•titania, titania•zirconia, zeolite and diatomaceous earth; and clay and active carbon. These supports may be used individually or in combination of two or more kinds.

When the Group VIII element, etc., is immobilized on a support, i.e., when the catalyst is a supported catalyst immobilizing the Group VIII element (and second element group and/or third element group) on a support, it becomes easier to separate the catalyst from the reaction liquid after the reaction. In addition, the catalytic activity can be improved. Note that, the second element group and/or third element group, instead of being immobilized on a support, may be subjected to a reaction by adding a compound including the second element group and/or a compound including the third element group into the reaction liquid together with a supported catalyst immobilizing the Group VIII element.

Even though the method of preparing the catalyst is not particularly limited, the following describes how the catalyst is prepared, for example, when it is a supported catalyst immobilizing the Group VIII element (and second element group and/or third element group) on a support.

As to how the Group VIII element is immobilized on a support is not particularly limited, and various conventional supporting methods, for example, such as impregnation method, precipitation method, ion exchange method, deposition method, vapor deposition method, deposition/precipitation method, and co-precipitation method can be adopted. Of these immobilizing methods, deposition method, vapor deposition method, deposition/precipitation method, and co-precipitation method are more preferable. When adopting these methods, the Group VIII element is immobilized in the form of fine particles on a support, which increases the number of active points of the catalyst, thus further improving the catalytic activity.

The following describes one example of a specific method of preparing a catalyst which includes palladium as the Group VIII element and gold as the second element group, using the deposition/precipitation method. First, a water soluble palladium compound and water soluble gold compound are dissolved in water. Here, heat may be applied as required. Also, the pH of the aqueous solution may be appropriately adjusted as required by adding an alkali compound so that the palladium hydroxide and gold hydroxide can deposit and precipitate in the form of fine particles. Then, a support is added to the aqueous solution, and the aqueous solution is stirred as required for a predetermined period of time. Thereafter, a support (support immobilizing palladium hydroxide and gold hydroxide) is removed to be washed and dried. Then, the support is calcined at a predetermined temperature as required, thereby preparing the catalyst. Note that, the order of supporting the palladium and gold on a support is not particularly limited, and they may be supported simultaneously or one after another.

When the catalyst exists as a supported catalyst, the content of the Group VIII element is appropriately set, for example, in accordance with a composition of a desired catalyst or a combination of the second element group and/or third element group which are used as required, for which a range of 0.01% by weight to 20% by weight is preferable, and a range of 0.1% by weight to 5% by weight is more preferable with respect to the total weight of the catalyst. The content of the Group VIII element below these ranges makes the catalytic activity considerably lower and is not preferable. On the other hand, the content exceeding these ranges increases the production cost of the catalyst, which makes it difficult to efficiently and inexpensively produce the (acyloxyalkyl)aromatic carboxylic acids in industrial applications.

When the catalyst exists as a supported catalyst, the content of the second element group, which is used as required is appropriately is set, though not particularly limited, for example, in accordance with a combination with the Group VIII element. For example, when the second element group is gold, a range of 0.01% by weight to 20% by weight is preferable, and a range of 1% by weight to 10% by weight is more preferable with respect to the total weight of the catalyst. The content of gold, i.e., the second element group, below these ranges makes the catalytic activity which is obtained by including the second element group considerably lower. Specifically, the reaction rate slows down and the target product (acyloxyalkyl)aromatic carboxylic acids may not be obtained efficiently. Further, the content exceeding the above ranges increases the production cost of the catalyst, which makes it difficult to produce (acyloxyalkyl) aromatic carboxylic acids inexpensively.

When the catalyst exists as a supported catalyst, the content of the third element group, which is used as required is appropriately is set, though not particularly limited, for example, in accordance with a composition of the target catalyst or a combination with the Group VIII element, and a range of 0.0001% by weight to 10% by weight is preferable, and a range of 0.001% by weight to 2% by weight is more preferable. The content of the third element group below these ranges makes the reaction rate which is obtained by including the third element group considerably slower.

The oxidation reaction of the alkyl substituted aromatic compounds and carboxylic acids in the presence of the catalyst gives the (acyloxyalkyl)aromatic carboxylic acids. The oxidation reaction is carried out in a liquid phase or gaseous phase in the presence of oxygen gas (molecular oxygen). The oxygen gas may be diluted with an inert gas such as nitrogen gas, helium gas, argon gas, or carbon dioxide gas. Further, air may be used as the oxygen gas. The supply method of oxygen gas into the reaction system is not particularly limited.

The oxidation reaction may be any of a continuous type, batch type, and semibatch type, and is not particularly limited. For example, when the reaction is of a batch type, the catalyst is added into the reaction apparatus together with the raw material, and in the case of a continuous type, for example, the catalyst is injected into the reaction apparatus in advance, or it is added into the reaction apparatus continuously with the raw material. Thus, the catalyst may be used in any of a fixed bed, fluidized bed, and suspension bed.

The amount of catalyst used with respect to the alkyl substituted aromatic compounds as a reaction substrate is not particularly limited, and it is set in accordance with the types and/or combination of alkyl substituted aromatic compounds and carboxylic acids, composition of the catalyst, and reaction conditions, etc.

Reaction conditions such as reaction temperature, reaction pressure, and reaction time are not particularly limited, and they are set in accordance with the types and/or combination of alkyl substituted aromatic compounds and carboxylic acids, and a composition of the catalyst, and a reaction temperature in a range of 80° C. to 200° C. is preferable. A reaction temperature below 80° C. makes the reaction rate considerably slow and the oxidation reaction may not be carried out efficiently. On the other hand, a reaction temperature exceeding 200° C. causes side reactions such as combustion reaction and excessive oxidation reaction (e.g., generation of dicarboxylic acids) more frequently, and the oxidation reaction may not be carried out efficiently. Also, corrosion of the reaction apparatus may be incurred by the carboxylic acids.

The reaction pressure may be either ordinary pressure (atmospheric pressure) or applied pressure, and when using oxygen gas (oxygen gas undiluted with inert gas) in the oxidation reaction, a pressure in a range of ordinary pressure to $4.9 \times 10^6$ Pa (gauge pressure) is preferable, and when using air in the oxidation reaction, a pressure in a range of ordinary pressure to $9.8 \times 10^6$ Pa (gauge pressure) is preferable. A pressure exceeding $9.8 \times 10^6$ Pa would require a reactor, etc., which can withstand high pressure, and from an industry point of view it is not preferable.

When the alkyl substituted aromatic compounds and/or carboxylic acids are liquid, the oxidation reaction does not necessarily require a solvent. However, when these compounds cannot be uniformly mixed together, or when the oxidation reaction is violent, the reaction liquid may be diluted with a solvent which is inactive toward the oxidation reaction.

By the oxidation reaction, a reaction resultant containing (acyloxyalkyl)aromatic carboxylic acids is obtained. In addition to the target product (acyloxyalkyl) aromatic carboxylic acids, the resultant also contains unreacted alkyl substituted aromatic compounds and carboxylic acids, the catalyst, reaction intermediate, and solvent (when used), etc. The catalyst can easily be separated, for example, by filtering the resultant. In the case where the catalytic activity of the catalyst thus separated and recovered has been decreased (deteriorated), for example, by absorption of organic substances, etc., the catalyst can easily be regenerated (reactivated), for example, by washing the catalyst with a solvent or by calcining the catalyst again. The catalyst separated and recovered and the catalyst reactivated can be reused in the oxidation reaction. Note that, the catalyst can be separated and regenerated by various conventionally known methods, and they are not particularly limited.

The (acyloxyalkyl)aromatic carboxylic acids can easily be isolated, for example, by distilling the reaction resultant from which the catalyst has been removed, or by crystallization using a solvent in which the (acyloxyalkyl)aromatic carboxylic acids do not dissolve. The (acyloxyalkyl) aromatic carboxylic acids thus isolated are used as a raw material in the method of producing the (hydroxyalkyl) alicyclic carboxylic acids. Note that, the (acyloxyalkyl) aromatic carboxylic acids can be isolated by various conventionally known methods and the method is not particularly limited.

Further, the alkyl substituted aromatic compounds and carboxylic acids which did not undergo reaction, the reaction intermediate, and the solvent (when used) can be separated and recovered, for example, when isolating the (acyloxyalkyl)aromatic carboxylic acids. The compounds, etc., which did not undergo reaction thus recovered can be reused as a raw material of the oxidation reaction, thus producing the (acyloxyalkyl)aromatic carboxylic acids further efficiently and inexpensively.

The (hydroxyalkyl)alicyclic carboxylic acids can be obtained (1) by hydrogenation of the (acyloxyalkyl)aromatic carboxylic acids, or, preferably the aromatic ring of the (acyloxyalkyl)aromatic carboxylic acids synthesized by the above method, followed by hydrolysis of the product (acyloxyalkyl)alicyclic carboxylic acids by hydrolysis, or, alternatively, (2) by hydrolysis of the (acyloxyalkyl) aromatic carboxylic acids, or, preferably the (acyloxyalkyl) aromatic carboxylic acids synthesized by the above method, followed by hydrogenation of the aromatic ring of the product (hydroxyalkyl)aromatic carboxylic acids by hydrogenation.

The method of hydrogenating the aromatic ring of the (acyloxyalkyl)aromatic carboxylic acids is not particularly limited and any conventionally known method can be adopted. For example, the aromatic ring of the (acyloxyalkyl)aromatic carboxylic acids can easily be hydrogenated with the use of the (acyloxyalkyl)aromatic carboxylic acids and an equivalent or greater amount of hydrogen and by allowing the (acyloxyalkyl)aromatic carboxylic acids to react with hydrogen using a hydrogenation catalyst.

The hydrogen is used in excess of the (acyloxyalkyl) aromatic carboxylic acids, and the exact mole ratio of hydrogen with respect to the (acyloxyalkyl)aromatic carboxylic acids, and the supply method and partial pressure, etc., of hydrogen are not particularly limited.

The hydrogenation reaction is carried out in a liquid phase or gaseous phase in the presence of hydrogen gas. The hydrogen gas may be diluted with an inert gas such as nitrogen gas, helium gas, or argon gas.

Specifically, as the reducing catalyst, for example, the following compounds but not limited to these are available: Pt group metal supporting catalysts immobilizing a Pt group metal element such as palladium, platinum, rhodium, ruthenium, and iridium on a support; Pt group metal oxides such as palladium oxides, platinum oxides, rhodium oxides, ruthenium oxides and iridium oxide; Pt group metal simple substance such as palladium black, platinum black, rhodium black, and ruthenium black; Raney catalyst such as Raney nickel, Raney cobalt, Raney ruthenium, Raney rhodium; and base metal supporting catalysts supporting a base metal element on a support. These reducing catalysts may be used individually or in combination of two or more kinds.

The support is not particularly limited but inorganic compounds are preferable and porous inorganic compounds are most preferable. Specifically, as the support, for example, the following compounds but not limited to these are available: isocrystalline or amorphous metal oxides or composite metal oxides such as silicon oxide (silica), aluminium oxide (alumina), titanium oxide (titania), zirconium oxide (zirconia), magnesium oxide (magnesia), silica•alumina, silica•titania, titania, zirconia, zeolite, and diatomaceous earth; and clay and active carbon. These supports may be used individually or in combination of two or more kinds. When the reducing catalyst is a supporting catalyst, the reducing catalyst can be easily separated from the reaction mixture after the reaction.

The preparation method of the reducing catalyst is not particularly limited. For example, the method of supporting the Pt group metal element and/or base metal element on a support may be carried out by conventionally known preparation methods, for example, such as impregnation method.

When the catalyst is a supporting catalyst, the content, etc., of the Pt group metal element and/or base metal element is not particularly limited and it is set appropriately, for example, in accordance with the types of (acyloxyalkyl) aromatic carboxylic acids and metal element immobilized on a support, and the reaction conditions. The method of preparing Raney catalyst may also be carried out by any conventionally known method.

The amount of the reducing catalyst used with respect to the (acyloxyalkyl)aromatic carboxylic acids as a reaction substrate is not particularly limited and it is set, for example, in accordance with the composition of the reducing catalyst, reaction conditions, and supply method and partial pressure of the hydrogen. However, the amount of metal element used with respect to the (acyloxyalkyl)aromatic carboxylic acids is preferably in a range of 0.00001 mole % to 0.1 mole %. The amount of the reducing catalyst used with respect to the (acyloxyalkyl)aromatic carboxylic acids below this range makes the catalytic activity considerably lower and is not preferable. On the other hand, the amount of the reducing catalyst used with respect to the (acyloxyalkyl)aromatic carboxylic acids above this range increases the production cost, and the (acyloxyalkyl)alicyclic carboxylic acids and the target product (hydroxyalkyl)alicyclic carboxylic acids may not be produced inexpensively.

Note that, the specific method of driving the hydrogenation reaction is not particularly limited and various conventionally known methods can be adopted. The hydrogenation reaction may be any of a continuous type, batch type, and semibatch type, and it is not particularly limited. For example, when the reaction is of a batch type, the catalyst is added to the reaction apparatus together with the raw material, and, for example, when the reaction is of a continuous type, the catalyst is injected into the reaction apparatus in advance, or the catalyst is added to the reaction apparatus continuously with the raw material. Thus, the catalyst may be used in any of a fixed bed, fluidized bed, and suspension bed.

Reaction conditions such as reaction temperature, reaction pressure, and reaction time are not particularly limited and they are set in accordance with the type of the (acyloxyalkyl)aromatic carboxylic acids, the type of the reducing catalyst, and the supply method and partial pressure of the hydrogen, etc., and a reaction temperature in a range of ordinary temperature to 250° C. is preferable, and a range of 50° C. to 200° C. is more preferable. A reaction temperature below ordinary temperature (25° C.) slows down the reaction rate considerably, and the hydrogenation reaction may not be carried out efficiently. On the other hand, a reaction temperature exceeding 250° C. causes side reactions more frequently, and the hydrogenation reaction may not be carried out efficiently. The reaction pressure is not particularly limited and may be either ordinary pressure (atmospheric pressure) or applied pressure, and a range of 0.098 Mpa to 24.5 MPa (gauge pressure) is preferable, and a range of 0.098 MPa to 14.7 MPa (gauge pressure) is more preferable. However, a higher reaction pressure would require a reactor, etc., which can withstand high pressure, and from an industry stand point, a reaction pressure below 9.8 MPa (gauge pressure) is further preferable.

When the (acyloxyalkyl)aromatic carboxylic acids are liquid under the above reaction conditions, the hydrogenation reaction does not necessarily require a solvent. However, for example, when the hydrogenation reaction is violent depending on reaction conditions and reaction type, the reaction liquid may be diluted as required with a solvent which is inactive toward the reaction. For example, the hydrogenation reaction can be driven with ease by mixing the (acyloxyalkyl)aromatic carboxylic acids with an appropriate amount of solvent, followed by addition of a reducing catalyst and replacement of the reaction system with an inert gas, and thereafter by drawing a hydrogen gas, and by applying heat as required.

Specifically, as such a solvent, for example, the following compounds but not limited to these are available: water; alcohols having a carbon number of 1 to 6, such as methanol, ethanol, n-propylalcohol, isopropyl alcohol, n-butyl alcohol, isobutyl alcohol, sec-butyl alcohol, and tert-butyl alcohol; ethers such as isopropyl ether, tetrahydrofuran, and dioxane; and saturated hydrocarbon compounds having a carbon number of 1 to 6 such as pentane, hexane, cyclohexane. These solvents may be used individually or in combination of two or more kinds.

By the hydrogenation reaction, a reaction liquid containing (acyloxyalkyl)alicyclic carboxylic acids, which are precursors (product intermediates) of the (hydroxyalkyl) alicyclic carboxylic acids in accordance with the present invention is obtained. In addition to the (acyloxyalkyl) alicyclic carboxylic acids, the reaction liquid also contains unreacted (acyloxyalkyl)aromatic carboxylic acids and reducing catalyst, and a solvent (when used), etc.

The reducing catalyst can easily be separated, for example, by filtering the reaction liquid. In the case where the catalytic activity of the catalyst thus separated and recovered has been dropped (deteriorated), for example, by absorption of organic substances, etc., the reducing catalyst can easily be regenerated (reactivated), for example, by washing the reducing catalyst with a solvent or by calcining the reducing catalyst again. The reducing catalyst separated and recovered and the reducing catalyst regenerated can be reused in the hydrogenation reaction. Note that, the reducing catalyst can be separated and regenerated by various conventionally known methods and they are not particularly limited.

The (acyloxyalkyl)alicyclic carboxylic acids can easily be isolated, for example, by distilling or crystallizing the reaction liquid from which the reducing catalyst has been removed. The (acyloxyalkyl)alicyclic carboxylic acids thus isolated are purified as required. Note that, the isolation method and purification method of the (acyloxyalkyl) alicyclic carboxylic acids may be carried out by various conventionally known methods and they are not particularly limited.

Further, the unreacted (acyloxyalkyl)aromatic carboxylic acids, and the solvent (when used) can be separated and recovered, for example, when isolating the acyloxyalkyl alicyclic carboxylic acids. The compounds, etc., which did not undergo reaction thus recovered can be reused as a raw material of the hydrogenation reaction. As a result, it is possible to produce the (acyloxyalkyl)alicyclic carboxylic acids and thus the (hydroxyalkyl)alicyclic carboxylic acids further efficiently and inexpensively. Note that, the separation method and recovering method of the (acyloxyalkyl) aromatic carboxylic acids and the solvent (when used) are not particularly limited.

The (hydroxyalkyl)alicyclic carboxylic acids in accordance with the present invention can easily be obtained by hydrolyzing their precursors (acyloxyalkyl)alicyclic carboxylic acids.

The (acyloxyalkyl)alicyclic carboxylic acids used in the above reaction are not particularly limited as long as they include within the same molecule an alicyclic compound group of two or greater valency having six or more carbon atoms, and a substituent such as acyloxyalkyl group and carboxyl group, and, specifically, the (acyloxyalkyl) alicyclic carboxylic acids have a structure which is represented by, for example, the following General Formula (2)

$$R^6COO-CR^1R^2-Z-COOH \quad (2)$$

(where Z is an alicyclic compound of two or greater valency having six or more carbon atoms, $R^1$ is a hydrogen atom or alkyl group having a carbon number of 1 to 3, $R^2$ is a hydrogen atom, alkyl group having a carbon number of 1 to 3, or —$OCOR^5$ group, $R^5$ is an alkyl group having a carbon number of 1 to 4, and $R^6$ is an alkyl group having a carbon number of 1 to 6, alkenyl group having a carbon number of 1 to 6, alkynyl group having a carbon number of 1 to 6, or a benzene ring, which may or may not include a substituent).

More specifically, the alicyclic compound group of two or greater valency having six or more carbon atoms indicates an alicyclic compound having six or more carbon atoms, i.e., a group of two or greater valency which results from removal of two or more hydrogen atoms from an alicyclic compound of a six or greater membered ring, and further specifically, it indicates a hydrogenated product of the aromatic ring, and in the present invention, it indicates a group (monocyclic or condensed polycyclic aliphatic compound group) which results from hydrogenation of a carbocyclic aromatic ring of two or greater valency (monocyclic or condensed polycyclic aromatic ring) or heterocyclic aromatic ring of two or greater valency (monocyclic or condensed polycyclic heterocyclic aromatic compound group). More specifically, it indicates a group having a structure which results from hydrogenation of a benzene ring, condensed ring such as a naphthalene ring, or heterocyclic ring such as a pyridine ring from which two or more hydrogen atoms have been removed.

A group having such a structure includes: a group of two or greater valency which results from removal of two or more hydrogen atoms from cycloalkane having six or more carbon atoms, such as cyclohexane and decalin, and its derivative (including condensed polycyclic compound), and a group of two or greater valency which results from removal of two or more hydrogen atoms from a heterocyclic compound of a six or greater membered ring (monocyclic or condensed polycyclic aliphatic heterocyclic compound) such as piperidine ring. The (acyloxyalkyl)alicyclic carboxylic acids may further include a functional group which is inactive toward the hydrolysis reaction, etc., to be described later.

Specifically, as such (acyloxyalkyl)alicyclic carboxylic acids, for example, (acyloxyalkyl)cyclohexane carboxylic acids such as 2-, 3-, 4-acetoxymethyl cyclohexane carboxylic acids are available but not limited to these.

The method of hydrolyzing the (acyloxyalkyl)alicyclic carboxylic acids is not particularly limited, and any conventionally known method can be adopted. The hydrolysis can be easily carried out, for example, by the method using an aqueous solution including the (acyloxyalkyl)alicyclic carboxylic acids and an equivalent or greater amount of alkali compound, or by a method using an acid catalyst.

For example, in the method using an acid catalyst, the hydrolysis reaction can be driven easily by mixing the (acyloxyalkyl)alicyclic carboxylic acids and an equivalent or greater amount of water, followed by addition of an acid catalyst into the reaction system, and by applying heat as required.

Specifically, as such an acid catalyst, for example, the following compounds but not limited to these are available: homogeneous catalysts such as sulfuric acid, hydrochloric acid, nitric acid, heteropolyacid, and p-toluene sulfonic acid; and heterogeneous catalysts (solid acid catalysts) such as acidic ion exchange resin, zeolite, and clay. The amount of acid catalyst used with respect to the (acyloxyalkyl)alicyclic carboxylic acids is not particularly limited.

Reaction conditions such as reaction temperature, reaction pressure, and reaction time are not particularly limited and they are appropriately set depending on the type of the (acyloxyalkyl)alicyclic carboxylic acids, and the type of the alkali compound or acid catalyst, and a reaction temperature in a range of 30° C. to 160° C. is preferable, and a range of 50° C. to 140° C. is more preferable. A reaction temperature below 30° C. slows down the reaction rate considerably and the hydrolysis reaction may not be carried out efficiently. On the other hand, a reaction temperature exceeding 160° C. causes a side product (polymerized product, etc.) to generate more often by a side reaction such as a polymerization reaction, and the hydrolysis reaction may not be carried out efficiently. The reaction pressure may be any of reduced pressure, ordinary pressure (atmospheric pressure), and applied pressure, but a pressure in a range of ordinary temperature to $4.9 \times^5$ Pa (gauge pressure) is preferable.

By the hydrolysis reaction, an aqueous solution containing (hydroxyalkyl)alicyclic carboxylic acids is obtained. In addition to the target product (hydroxyalkyl)alicyclic carboxylic acids, the aqueous solution also contains unreacted (acyloxyalkyl)alicyclic carboxylic acids, and carboxylic acids such as monocarboxylic acid which were generated when preparing the (hydroxyalkyl)alicyclic carboxylic acids from the (acyloxyalkyl)alicyclic carboxylic acids, and the aqueous solution also contains a catalyst, etc., such as an acid catalyst depending on the reaction method.

The catalyst can easily be separated, for example, by filtering the reaction liquid. In the case where the catalytic activity of the catalyst separated and recovered has been decreased, for example, by absorption of organic substances, etc., the catalyst can easily be regenerated (reactivated), for example, by washing the catalyst with a solvent or by calcining the catalyst again. The catalyst (hydrolysis catalyst) such as an acid catalyst separated and recovered and the catalyst (hydrolysis catalyst) such as an acid catalyst regenerated can be reused in the hydrolysis reaction. Note that, the catalyst can be separated and regenerated by any conventionally known method and they are not particularly limited.

The (hydroxyalkyl)alicyclic carboxylic acids can be easily isolated, for example, by distilling or crystallizing the aqueous solution from which the catalyst has been removed. The (hydroxyalkyl)alicyclic carboxylic acids thus isolated are purified as required. Note that, the isolation method and purification method of the (hydroxyalkyl)alicyclic carboxylic acids are not particularly limited and they can be carried out by any conventionally known method.

Further, the unreacted (acyloxyalkyl)alicyclic carboxylic acids, and the carboxylic acids such as monocarboxylic acid, which were generated when preparing the (hydroxyalkyl) alicyclic carboxylic acids from the (acyloxyalkyl)alicyclic carboxylic acids can be separated and recovered, for example, when isolating the (hydroxyalkyl)alicyclic carboxylic acids.

The compounds, etc., i.e., the unreacted (acyloxyalkyl)alicyclic carboxylic acids may be purified as required and hydrolyzed again to obtain the (hydroxyalkyl)alicyclic carboxylic acids. That is, the (acyloxyalkyl)alicyclic carboxylic acids can be reused as a raw material of the hydrolysis reaction. Note that, the method of separating and recovering the carboxylic acids such as monocarboxylic acids, which were generated when preparing the (hydroxyalkyl)alicyclic carboxylic acids from the (acyloxyalkyl) alicyclic carboxylic acids are not particularly limited.

Further, the carboxylic acids, which were generated when preparing the (hydroxyalkyl)aromatic carboxylic acids from the (acyloxyalkyl)alicyclic carboxylic acids are separated and recovered, and after being purified as required, they may be used as a raw material of the (acyloxyalkyl)aromatic carboxylic acids in the reaction (oxidative esterification reaction) between the alkyl substituted aromatic compounds and the carboxylic acids.

As a result, the (hydroxyalkyl)alicyclic carboxylic acids can be produced further efficiently and inexpensively.

The following will describe the method of producing the (hydroxyalkyl)alicyclic carboxylic acids from the (acyloxyalkyl)aromatic carboxylic acids via the (hydroxyalkyl)aromatic carboxylic acids, i.e., the method (2).

The (hydroxyalkyl)aromatic carboxylic acids can be easily obtained by hydrolysis of the (acyloxyalkyl)aromatic carboxylic acids. The hydrolysis reaction can easily be driven, for example, with the use of an aqueous solution including the (acyloxyalkyl)aromatic carboxylic acids and an equivalent or greater amount of an alkali compound, or with the use of an acid catalyst. Note that, the specific method of driving the hydrolysis reaction is not particularly limited and any conventionally known method can be adopted. For example, the hydrolysis reaction may be carried out by the same hydrolysis method as that of the (acyloxyalkyl)alicyclic carboxylic acids. For example, in the method using an acid catalyst, the hydrolysis reaction can easily be driven by mixing the (acyloxyalkyl)carboxylic acids with an appropriate amount of water, followed by addition of an acid catalyst in the reaction system, and by applying heat as required. In this case, even though the reaction conditions of the hydrolysis of the (acyloxyalkyl) aromatic carboxylic acids are the same as the reaction conditions of the hydrolysis reaction of the (acyloxyalkyl) alicyclic carboxylic acids, they are not particularly limited.

By the hydrolysis reaction, an aqueous solution containing the (hydroxyalkyl)aromatic carboxylic acids is obtained. In addition to the (hydroxyalkyl)aromatic carboxylic acids, the aqueous solution further contains unreacted (acyloxyalkyl)aromatic carboxylic acids, and the carboxylic acids such as monocarboxylic acid which were generated when preparing the (hydroxyalkyl)aromatic carboxylic acids from the (acyloxyalkyl)aromatic carboxylic acids, and the catalyst such as an acid catalyst depending on the reaction method.

The catalyst can be separated easily by filtering the reaction liquid. In the case where the catalytic activity of the catalyst has been decreased, for example, by absorption of an organic substances, etc., the catalyst separated and recovered can easily be regenerated (reactivated), for example, by washing the catalyst with a solvent or by calcining the catalyst again. The catalyst (hydrolysis catalyst) such as an acid catalyst separated and recovered and the catalyst (hydrolysis catalyst) such as an acid catalyst regenerated can be reused in the hydrolysis reaction. Note that, the catalyst can be separated and regenerated by any conventionally known method and they are not particularly limited.

The (hydroxyalkyl)aromatic carboxylic acids can easily be isolated, for example, by distilling or crystallizing the aqueous solution from which the catalyst has been removed. Also, the (hydroxyalkyl)aromatic carboxylic acids isolated are purified as required. Note that, the isolation method and purification method of the (hydroxyalkyl)aromatic carboxylic acids can be carried out by any conventionally known method and are not particularly limited.

Further, the unreacted (acyloxyalkyl)aromatic carboxylic acids, and the carboxylic acids such as monocarboxylic acids which were generated when preparing the (hydroxyalkyl)aromatic carboxylic acids from the (acyloxyalkyl)aromatic carboxylic acids can be separated and recovered, for example, when isolating the (hydroxyalkyl)aromatic carboxylic acids.

The compound which did not react, i.e., the (acyloxyalkyl)aromatic carboxylic acids are purified as required, and by performing the hydrolysis reaction again, (hydroxyalkyl)aromatic carboxylic acids can be obtained. That is, the (acyloxyalkyl)aromatic carboxylic acids can be reused as a raw material of the hydrolysis reaction. Note that, the separation and recovering methods of the (acyloxyalkyl)aromatic carboxylic acids, and the carboxylic acids such as monocarboxylic acids which were generated when preparing the (hydroxyalkyl)aromatic carboxylic acids from the (acyloxyalkyl)aromatic carboxylic acids are not particularly limited.

The carboxylic acids which were generated when preparing the (hydroxyalkyl)aromatic carboxylic acids from the (acyloxyalkyl)aromatic carboxylic acids are separated and recovered, and after being purified as required, they can be used as a raw material of the (acyloxyalkyl)aromatic carboxylic acids in the reaction (oxidative esterification reaction) between the alkyl substituted aromatic compounds and carboxylic acids.

As a result, it is possible to produce the (hydroxyalkyl) aromatic carboxylic acids, and thus the (hydroxyalkyl) alicyclic carboxylic acids further efficiently and inexpensively in industrial applications.

The (hydroxyalkyl)aromatic carboxylic acids are not particularly limited, but, specifically, has a structure which is represented, for example, by the following General Formula (4)

$$HO-CR^1R^2-Ar-COOH \quad (4)$$

(where Ar is an aromatic ring of two or greater valency, $R^1$ is a hydrogen atom or alkyl group having a carbon number of 1 to 3, $R^2$ is a hydrogen atom, alkyl group having a carbon number of 1 to 3, or $-OCOR^5$ group, and $R^5$ is an alkyl group having a carbon number of 1 to 4).

More, specifically, as the (hydroxyalkyl)aromatic carboxylic acids, for example, o-, m-, p-(hydroxyalkyl)benzoic acids, such as o-, m-, p-hydroxymethyl benzoic acids are available.

The (hydroxyalkyl)aromatic carboxylic acids can easily be obtained by hydrogenating (hydrogenation) the aromatic ring of the (hydroxyalkyl)aromatic carboxylic acids by the hydrogenation reaction.

The method of hydrogenating the aromatic ring of the (hydroxyalkyl)aromatic carboxylic acids is not particularly limited, and, for example, the reaction can be driven easily with the use of the (hydroxyalkyl) aromatic carboxylic acids and an equivalent or greater amount of hydrogen by allowing the (hydroxyalkyl)aromatic carboxylic acids to react with hydrogen using a hydrogenation catalyst (reducing catalyst).

Hydrogen is used in excess of the (hydroxyalkyl) aromatic carboxylic acids, and the specific mole ratio of the hydrogen with respect to the (hydroxyalkyl)aromatic carboxylic acids, and the supply method and partial pressure of the hydrogen are not particularly limited.

The hydrogenation reaction is carried out in a liquid phase or gaseous phase in the presence of a hydrogen gas. The hydrogen gas may be diluted with an inert gas such as nitrogen gas, helium gas, and argon gas.

The reducing catalyst is not particularly limited, and a catalyst which includes at least one of Pt group metal elements selected from the group consisting of rhodium and ruthenium is suitably adopted. Specifically, for example, a supporting catalyst which immobilizes at least one of rhodium and ruthenium on a support; oxides such as rhodium oxide and ruthenium oxide; a metal simple substance such as rhodium black and ruthenium black; and Raney catalysts such as Raney rhodium and Raney ruthenium are available. Of these compounds, the supporting catalyst is particularly preferable because of its superior catalytic activity and its ability to easily separate the reducing catalyst from the reaction liquid after the reaction. These reducing catalysts may be used individually or in combination of two or more kinds.

The support is not particularly limited but inorganic compounds are preferable and porous inorganic compounds are most preferable. Specifically, as such supports, for example, the following compounds but not limited to these are available: isocrystalline or amorphous metal oxides such as silica oxide (silica), aluminium oxide (alumina), titanium oxide (titania), zirconium oxide (zirconia), magnesium oxide (magnesia), silica-alumina, silica-titania, titania-zirconia, zeolite, and diatomaceous earth, or clay, and active carbon. These supports may be used individually or in combination of two or more kinds.

The amount of the reducing catalyst used with respect to the (hydroxyalkyl)aromatic carboxylic acids as a reaction substrate is not particularly limited and it is set, for example, depending on the composition of the reducing catalyst, the reaction conditions, and the supply method and partial pressure of the hydrogen, and it is preferably set so that the content of the metal element with respect to the (hydroxyalkyl)aromatic carboxylic acids is in a range of 0.00001 mole % to 0.1 mole %. The amount of the reducing catalyst used with respect to the (hydroxyalkyl)aromatic carboxylic acids below this range makes the catalytic activity considerably lower and is not preferable. On the other hand, the amount of the reducing catalyst used with respect to the (hydroxyalkyl)aromatic carboxylic acids exceeding the above range increases the production cost of the catalyst, and the target product (hydroxyalkyl)alicyclic carboxylic acids may not be produced inexpensively.

Note that, the specific method of driving the hydrogenation reaction is not particularly limited and any conventionally known method can be adopted. More specifically, the aromatic of the (hydroxyalkyl)aromatic carboxylic acids can be hydrogenated, for example, by the above described hydrogenating method of the aromatic ring of the (hydroxyalkyl)aromatic carboxylic acids. The hydrogenation reaction may be any of a continuous type, batch type, and semibatch type, and is not particularly limited. When the hydrogenation reaction is, for example, of a batch type, the reducing catalyst is added into the reaction apparatus together with the raw material, and when the reaction is, for example, of a continuous type, the reducing catalyst is injected into the reaction apparatus in advance, or it is continuously added into the reaction apparatus together with the raw material. Thus, the catalyst may be used in any of a fixed bed, fluidized bed, and suspension bed.

Reaction conditions such as reaction temperature, reaction pressure, and reaction time are not particularly limited and they are set appropriately depending on the type of the (hydroxyalkyl)aromatic carboxylic acids, the type of the reducing catalyst, and the supply method and partial pressure of the hydrogen, and a reaction temperature in a range of ordinary temperature to 250° C. is preferable and a range of 50° C. to 200° C. is more preferable. A reaction temperature below ordinary temperature (25° C.) slows down the reaction rate considerably and the hydrogenation reaction may not be carried out efficiently. On the other hand, a reaction temperature exceeding 250° C. causes side reactions more frequently and the hydrogenation reaction may not be carried out efficiently. The reaction pressure is not particularly limited and it may be ordinary pressure (atmospheric pressure) or applied pressure, and a range of 0.098 MPa to 24.5 MPa is preferable, and a range of 0.098 MPa to 14.7 MPa is more preferable. However, a higher reaction pressure would require a reactor which can withstand a high pressure, and from an industry point of view, a reaction pressure of 9.8 MPa (gauge pressure) or below is more preferable.

When the (hydroxyalkyl)aromatic carboxylic acids are liquid under the above reaction conditions, the hydrogenation reaction does not necessarily require a solvent. However, depending on the reaction conditions and reaction type, for example, when the hydrogenation reaction is violent, the reaction liquid may be diluted as required using a solvent which is inactive toward the reaction. For example, the hydrogenation reaction can be driven easily by mixing the (hydroxyalkyl)aromatic carboxylic acids with an appropriate amount of solvent, followed by addition of a reducing catalyst, and after replacing the reaction system with an inert gas, by drawing a hydrogen gas, followed by heating as required. As the solvent, the solvents as exemplified in the hydrogenation reaction of the (acyloxyalkyl)aromatic carboxylic acids can be used.

The conditions of the hydrogenation reaction using the reducing catalyst are such that compared with the conditions of the hydrogenation reaction of the (hydroxyalkyl)aromatic carboxylic acids using the reducing catalyst which has been conventionally used in the hydrogenation reaction of the (hydroxyalkyl)aromatic carboxylic acids, the reaction temperature and reaction pressure are relieved, thus producing the target product (hydroxyalkyl)alicyclic carboxylic acids efficiently and inexpensively in industrial applications.

The specific method of driving the hydrogenation reaction is not particularly limited and any conventionally known method can be adopted. Even though the reaction conditions will not be as desirable as those of the method as described above, the hydrogenation can be carried out by the conventionally known method which employs a catalyst other than the catalyst which is selected from the group consisting of rhodium and ruthenium as exemplified in the hydrogenation reaction of the (hydroxyalkyl)aromatic carboxylic acids, as the reducing catalyst of the hydrogenation reaction of the (hydroxyalkyl)aromatic carboxylic acids.

By the hydrogenation reaction, a reaction liquid containing the target product (hydroxyalkyl)alicyclic carboxylic acids is obtained. In addition to the target product (hydroxyalkyl)alicyclic carboxylic acids, the reaction liquid also contains the (hydroxyalkyl)aromatic carboxylic acids which did not undergo reaction, and the reducing catalyst, and the solvent (when used), etc.

The reducing catalyst can easily be separated, for example, by filtering the reaction liquid. When the catalytic activity of the reducing catalyst has been decreased, for example, by absorption of organic substances, etc., the reducing catalyst separated and recovered can easily be regenerated (reactivated), for example, by washing the reducing catalyst with a solvent, or by calcining the reducing catalyst again. The reducing catalyst separated and recovered or the reducing catalyst regenerated can be reused in the hydrogenation reaction. Note that, the reducing catalyst may be separated and regenerated by any conventionally known method and they are not particularly limited.

The (hydroxyalkyl)alicyclic carboxylic acids can easily be isolated, for example, by distillating or crystallizing the reaction liquid from which the reducing catalyst has been removed. Also, the (hydroxyalkyl)alicyclic carboxylic acids isolated are purified as required. Note that, the isolation method and purification method of the (hydroxyalkyl)alicyclic carboxylic acids are not particularly limited and they can be carried out by any conventionally known method.

Further, the (hydroxyalkyl)aromatic carboxylic acids which did not undergo reaction, and the solvent (when used) can be separated and recovered, for example, when isolating the (hydroxyalkyl)alicyclic carboxylic acids. The compounds, etc., which did not undergo reaction can be reused as a raw material in the hydrogenation reaction, thereby producing the (hydroxyalkyl)alicyclic carboxylic acids further efficiently and inexpensively. Note that, the separation method and recovering method of the (hydroxyalkyl)aromatic carboxylic acids and the solvent (when used) are not particularly limited.

With the producing method in accordance with the present invention, it is possible to produce the (hydroxyalkyl)alicyclic carboxylic acids such as (hydroxyalkyl)cyclohexane carboxylic acids with high yield, both efficiently and inexpensively in industrial applications by the hydrogenation reaction and hydrolysis reaction using the (acyloxyalkyl)aromatic carboxylic acids as a starting material.

The (hydroxyalkyl)alicyclic carboxylic acids which are produced by the producing method of the present invention are compounds which include within the same molecule an alicyclic compound group of two or greater valency having six or more carbon atoms, and a substituent such as a hydroxyalkyl group and carboxyl group, and, specifically, have a structure, but not limited to this, which is represented, for example, by the following General Formula (5)

$$HO-CR^1R^2Z-COOH \quad (5)$$

(where Z is an alicyclic compound group of two or greater valency having six or more carbon atoms, $R^1$ is a hydrogen atom or alkyl group having a carbon number of 1 to 3, $R^2$ is a hydrogen atom, alkyl group having a carbon number of 1 to 3, or $-OCOR^5$ group, and $R^5$ is an alkyl group having a carbon number of 1 to 4).

The alicyclic compound group of two or greater valency having six or more carbon atoms indicates an alicyclic compound having six or more carbon atoms, i.e., a group of two or greater valency which results from removal of two or more hydrogen atoms from an alicyclic compound of six or greater membered ring, and, more specifically, a hydride of the aromatic ring (hydroaromatic compound group), and in the present invention, it indicates a group (monocyclic or condensed polycyclic aliphatic compound group, and monocyclic or condensed polycyclic aliphatic heterocyclic compound group) having a structure which results from hydrogenation of a carbocyclic aromatic ring of two or greater valency (monocyclic or condensed polycyclic aromatic compound group) or heteroaromatic ring (monocyclic or condensed polycyclic heteroaromatic ring)

The group having such a structure includes, for example, a group of two or greater valency which results from removal of two or more hydrogen atoms from cycloalkane having six or more carbon atoms and its derivative (including condensed polycyclic compounds) such as cyclohexane, tetralin, and decalin; and a group of two or greater valency which results from removal of two or more hydrogen atoms from a heterocyclic compound of six or greater membered ring (monocyclic or condensed polycyclic aliphatic heterocyclic compound) such as piperidine ring. The (hydroxyalkyl)alicyclic carboxylic acids may also include a functional group which is inactive toward the hydrogenation reaction and hydrolysis reaction.

Further, the (acyloxyalkyl) aromatic carboxylic acids as a raw material may be produced by partially oxidizing the alkyl substituted aromatic compounds and carboxylic acids in the presence of oxygen with a catalyst including an element which belongs to Group VIII of the periodic table, in which case the (hydroxyalkyl)alicyclic carboxylic acids such as (hydroxyalkyl)cyclohexane carboxylic acids can be produced both efficiently and inexpensively in industrial applications, for example, with the use of an inexpensive alkyl substituted aromatic compound, such as xylene, which can easily be obtained industrially. More specifically, with the use of p-xylene as a starting material, the 4-hydroxymethyl cyclohexane carboxylic acid can be produced efficiently and inexpensively in industrial applications.

Namely, with the described method, for example, with the use of xylene and acetic acid as starting materials, which can easily be obtained industrially, the hydroxymethyl cyclohexane carboxylic acids can be produced inexpensively in industrial applications by producing hydroxymethyl cyclohexane carboxylic acids from acetoxymethyl benzoic acid via acetoxymethyl cyclohexane carboxylic acid, or by producing hydroxymethyl cyclohexane carboxylic acid from acetoxymethyl benzoic acid via hydroxymethyl benzoic acid.

(1) The (hydroxyalkyl)cyclohexane carboxylic acids, which are one type of the (hydroxyalkyl)alicyclic carboxylic acids produced by the producing method of the present invention, and (2) the precursors (intermediates for producing the (hydroxyalkyl)alicyclic carboxylic acids) of the (hydroxyalkyl)cyclohexane carboxylic acids, the (hydroxyalkyl)aromatic carboxylic acids as well as the (acyloxyalkyl)cyclohexane carboxylic acids which are one type of the (acyloxyalkyl)alicyclic carboxylic acids, and (3) the (acyloxyalkyl)aromatic carboxylic acids, which are used as a raw material (starting material, or intermediate for producing the (hydroxyalkyl)alicyclic carboxylic acids in a reaction in which the starting material is the alkyl substituted aromatic compounds) are all industrially highly useful compounds as a raw material of synthetic fiber, synthetic resin (particularly, heat resistant polymer), and thermoplastic agent, and, for example, as a raw material for producing a homo-polymer or co-polymer with ethylene glycols, etc., of such compounds.

As described, the producing method of the (hydroxyalkyl)alicyclic carboxylic acids in accordance with the present invention is the method in which a hydrogenation reaction and hydrolysis reaction are carried out using the (acyloxyalkyl)aromatic carboxylic acids as a starting material. Specifically, it is a method in which the (acyloxyalkyl) aromatic carboxylic acids are subjected to hydrogenation, followed by hydrolysis, or, alternatively, subjected to hydrolysis followed by hydrogenation.

More specifically, a first producing method of (hydroxyalkyl)alicyclic carboxylic acids in accordance with the present invention includes the steps of (i) producing (acyloxyalkyl)alicyclic carboxylic acids by hydrogenation of an aromatic ring of (acyloxyalkyl)aromatic carboxylic acids; and (ii) subjecting the (acyloxyalkyl)alicyclic carboxylic acids obtained in step (i) to hydrolysis.

This method provides for a new method of producing the (hydroxyalkyl)alicyclic carboxylic acids, in which the (hydroxyalkyl)alicyclic carboxylic acids such as the (hydroxyalkyl)cyclohexane carboxylic acids are produced by a hydrogenation reaction (hydrogenation of aromatic ring) and hydrolysis reaction using the (acyloxyalkyl) aromatic carboxylic acids as a starting material. With this method, it is possible to efficiently and inexpensively produce in industrial applications the (hydroxyalkyl)aliphatic carboxylic acids such as (hydroxyalkyl)cyclohexane carboxylic acids, which are industrially highly useful compounds as a raw material (e.g., raw material for producing a homo-polyester or co-polyester with ethylene glycols, etc.) of, for example, paint or synthetic fiber of polyester, or synthetic resin.

Further, by hydrogenation of the aromatic ring of the (acyloxyalkyl)aromatic carboxylic acids, it is possible to efficiently and inexpensively produce in industrial applications the (acyloxyalkyl)alicyclic carboxylic acids, for example, such as the (acyloxyalkyl)alicyclic carboxylic acids as represented by General Formula (2), which are the precursors (product intermediates) of the (hydroxyalkyl) alicyclic carboxylic acids.

The (acyloxyalkyl)alicyclic carboxylic acids are industrially highly useful compounds as a raw material of, for example, paint or synthetic fiber of polyester, or synthetic resin, and thus with the use of the (acyloxyalkyl)alicyclic carboxylic acids, it is possible to efficiently and inexpensively produce in industrial applications the (hydroxyalkyl) alicyclic carboxylic acids such as (hydroxyalkyl) cyclohexane carboxylic acids, which are industrially highly useful compounds as a raw material of, for example, paint or synthetic fiber of polyester, or synthetic resin.

In order to produce the (hydroxyalkyl)alicyclic carboxylic acids further efficiently and further inexpensively in industrial applications, it is preferable that the (acyloxyalkyl) alicyclic carboxylic acids be produced by the described method. However, (acyloxyalkyl)alicyclic carboxylic acids other than those obtained from the described producing method may also be used. In the present invention, by the hydrolysis of the (acyloxyalkyl)alicyclic carboxylic acids, the (hydroxyalkyl)alicyclic carboxylic acids such as (hydroxyalkyl)cyclohexane carboxylic acids can be obtained with higher yield than the conventional yield by a very simple method of hydrolyzing the (acyloxyalkyl) alicyclic carboxylic acids. Thus, with this method, it is possible to efficiently and inexpensively produce in industrial applications the (hydroxyalkyl)alicyclic carboxylic acids, which are industrially highly useful compounds as a raw material of, for example, paint or synthetic fiber of polyester, or synthetic resin.

Further, a second producing method of (hydroxyalkyl) alicyclic carboxylic acids in accordance with the present invention includes the steps of (i) producing (hydroxyalkyl) aromatic carboxylic acids by hydrolysis of (acyloxyalkyl) aromatic carboxylic acids; and (ii) subjecting an aromatic ring of the (hydroxyalkyl)aromatic carboxylic acids obtained in step (i) to hydrogenation.

With this method, the (hydroxyalkyl)aromatic carboxylic acids, which are the precursors (product intermediates) of the (hydroxyalkyl)alicyclic carboxylic acids, can be produced with higher yield than the conventional yield by a very simple method of hydrolysis. Namely, with the above method, it is possible to efficiently and inexpensively produce in industrial applications the (hydroxyalkyl)aromatic carboxylic acids, and, by extension, the target product (hydroxyalkyl)cyclic aromatic carboxylic acids further efficiently and further inexpensively in industrial applications. Thus, the method provides for a new method of producing the (hydroxyalkyl)alicyclic carboxylic acids such as (hydroxyalkyl)cyclohexane carboxylic acids by a hydrolysis reaction and hydrogenation reaction using the (acyloxyalkyl)aromatic carboxylic acids as a starting material.

Further, by hydrolysis of the (acyloxyalkyl)aromatic carboxylic acids, it is possible to efficiently and inexpensively produce in industrial applications the (hydroxyalkyl) aromatic carboxylic acids, which are the precursors (product intermediates) of the (hydroxyalkyl)alicyclic carboxylic acids.

The (hydroxyalkyl)aromatic carboxylic acids are industrially highly useful compounds as a raw material of, for example, paint or synthetic fiber of polyester, or synthetic resin, and thus with the (hydroxyalkyl)aromatic carboxylic acids, it is possible to efficiently and inexpensively produce in industrial applications the (hydroxyalkyl)alicyclic carboxylic acids such as (hydroxyalkyl)cyclohexane carboxylic acids, which are industrially highly useful compounds as a raw material of, for example, paint or synthetic fiber of polyester, or synthetic resin.

In order to produce the (hydroxyalkyl)alicyclic carboxylic acids further efficiently and further inexpensively in industrial applications, it is preferable that the (hydroxyalkyl) aromatic carboxylic acids be produced by the described method. However, the (hydroxyalkyl)aromatic carboxylic acids which were obtained by a method other than the described method may also be used. In the present invention, as the catalyst to be used in hydrogenation of the aromatic ring of the (hydroxyalkyl)aromatic carboxylic acids, a catalyst which includes at least one kind of element which is selected from the group consisting of rhodium and ruthenium is used, by which, compared with the conditions of the hydrogenation of the (hydroxyalkyl)aromatic carboxylic acids using a reducing catalyst which has been conventionally used in the hydrogenation reaction of (hydroxyalkyl) aromatic carboxylic acids, reaction temperature and reaction pressure are relieved, thus producing the target product (hydroxyalkyl)alicyclic carboxylic acids efficiently and inexpensively in industrial applications.

Further, by producing the (acyloxyalkyl)aromatic carboxylic acids by partially oxidizing alkyl substituted aromatic compounds which are represented by the following General Formula (1)

$$CHR^1 R^2 \text{—} Ar \text{—} (R^3) \qquad (1)$$

(where Ar is an aromatic ring of two or greater valency, $R^1$ is a hydrogen atom or alkyl group having a carbon number of 1 to 3, $R^2$ is a hydrogen atom, alkyl group having a carbon number of 1 to 3, or —$OCOR^5$ group, $R^3$ is an alkyl group having a carbon number of 1 to 4, —COOH group, —CHO group, —$CH_2R^4$ group, or —$COOR^5$ group, n is an integer of 1 to 5, $R^4$ is a halogen atom, —OH group, or —$OCOR^5$ group, and $R^5$ is an alkyl group having a carbon number of 1 to 4), and carboxylic acids in the presence of oxygen using a catalyst including an element which belongs to Group VIII of the periodic table, it is possible to efficiently and inexpensively produce in industrial applications the (acyloxyalkyl) aromatic carboxylic acids, which can easily be converted to the (hydroxyalkyl)aromatic carboxylic acids by hydrolysis, or the (acyloxyalkyl) aromatic carboxylic acids, which can easily be converted to the (acyloxyalkyl)alicyclic carboxylic acids by hydrogenation. Thus, for example, using the alkyl substituted aromatic compounds such as xylene, which can easily be obtained industrially and which are inexpensive as a starting material, and after obtaining the (acyloxyalkyl)aromatic carboxylic acids such as acetoxymethyl benzoic acid by the reaction between the alkyl substituted aromatic compounds and carboxylic acids such as acetic acid in the presence of oxygen, the (acyloxyalkyl)aromatic carboxylic acids thus obtained can be used to produce the (hydroxyalkyl) alicyclic carboxylic acids such as hydroxymethylcyclohexane carboxylic acids. Further, the carboxylic acids such as acetic acid, which are generated when obtaining the (hydroxyalkyl)alicyclic carboxylic acids such as hydroxymethylcyclohexane carboxylic acids from the (acyloxyalkyl)aromatic carboxylic acids such as acetoxymethyl benzoic acids can be reused in the reaction between the alkyl substituted aromatic compounds such as xylene and the carboxylic acids. Thus, the (hydroxyalkyl)alicyclic carboxylic acids can be produced further efficiently and further inexpensively in industrial applications.

PREFERRED EMBODIMENTS OF THE PRESENT INVENTION

The following will describe the present invention in more detail but the invention is not to be limited by the following descriptions by any ways.

EXAMPLE 1

0.22 g of tetrachloroauric (III) acid·4 hydrate as a compound containing a second element group was dissolved in 200 ml of water, and after heating to 60° C., the pH was adjusted to 8.5 using an aqueous solution of sodium hydroxide. Then, 0.062 g of tetraammine palladium dichloride as a compound containing a Group VIII element was added to the aqueous solution and was dissolved therein, thus preparing an aqueous solution of tetrachloroauric (III) acid-tetraammine palladium dichloride. To the aqueous solution thus obtained was added 5 g of titanium oxide (provided by Norton K.K.) as a support at 60° C., and the mixture was stirred for an hour at the same temperature to suspend the titanium oxide, and precipitates of palladium and gold were immobilized on the surface of the suspended titanium oxide.

Thereafter, the suspension liquid was filtered, and the filter cake, i.e., the immobilized paradium-gold-titanium was water washed and was dried for 8 hours at 120° C. Then, the immobilized complex was calcined in air for 3 hours at 400° C. to obtain a titanium oxide supported paradium-gold catalyst ("catalyst (1)" hereinafter). The supported amount (content) of the palladium and the supported amount (content) of the gold in catalyst (1) were 0.5% by weight and 2.0% by weight, respectively.

Then, using the catalyst (1), oxidation reaction of alkyl substituted aromatic compounds was carried out. Namely, to a 100 ml autoclave were added 2.0 g of catalyst (1) prepared, 5.0 g of p-xylene as the alkyl substituted aromatic compounds (reaction substrate), and 24.0 g of acetic acid as the carboxylic acid, and the autoclave was sealed after adding 20 mg of bismuth acetate oxide as a compound containing a second element group and 0.2 g of potassium acetate as a compound containing a third element group. Thereafter, oxygen gas was drawn into the autoclave, and after increasing the internal pressure to $9.8 \times 10^5$ Pa (gauge pressure), the autoclave was heated to 140° C. to allow an oxidation reaction for 2 hours with stirring at 700 rpm. Thus, the catalyst in accordance with the present invention is made up of catalyst (1), bismuth acetate oxide, and potassium acetate.

After the reaction was finished, the autoclave was cooled. Then, the contents therein were taken out and the catalyst (1) was removed, and the composition of the resultant (reaction mixture) was analyzed by gas chromatography and liquid chromatography. The analysis revealed that the resultant contained 2.59 g (yield of 28.5 mole %) of p-acetoxymethyl benzoic acid as the (acyloxyalkyl)aromatic carboxylic acids. The resultant also contained 3.54 g (yield of 34.0 mole %) of p-xylylenediacetate, which is the precursor (reaction intermediate) of the p-acetoxymethyl benzoic acid as the (acyloxyalkyl)aromatic carboxylic acids, and 1.26 g (yield of 16.4 mole %) of p-methylbenzylacetate.

EXAMPLE 2

The oxidation reaction was carried out under the same reaction conditions as those of Example 1 except that 5 g of m-xylene (alkyl substituted aromatic compound) was used instead of p-xylene. After the reaction was finished, the composition of the reaction mixture was analyzed by gas chromatography, which revealed that the resultant contained 2.47 g (yield of 27.8 mole %) of m-acetoxymethyl benzoic acid as the (acyloxyalkyl)aromatic carboxylic acids. The reaction liquid also contained 3.10 g (yield of 29.8 mole %) of m-xylene diacetate as a reaction intermediate, and 1.34 g (yield of 17.4 mole %) of m-methylbenzyl acetate.

EXAMPLE 3

The oxidation reaction was carried out under the same reaction conditions as those of Example 1 except that 5 g of p-xylylenediacetate (alkyl substituted aromatic compound) was used instead of p-xylene. After the reaction was finished, the composition of the reaction mixture was analyzed by liquid chromatography, which revealed that the reaction mixture contained 1.95 g (yield of 44.7 mole %) of p-acetoxymethyl benzoic acid.

EXAMPLE 4

The oxidation reaction was carried out under the same reaction conditions as those of Example 1 except that 5 g of p-methylbenzyl acetate (alkyl substituted aromatic compound) was used instead of p-xylene. After the reaction was finished, the composition of the reaction mixture was analyzed by gas chromatography and liquid chromatography, which revealed that the reaction liquid contained 2.85 g (yield of 48.2 mole %) of p-acetoxymethyl benzoic acid. The reaction mixture also contained 0.73 g (yield of 10.8 mole %) of p-xylylenediacetate.

COMPARATIVE EXAMPLE 1

The same operation as that of Example 1 was carried out expect that tetraammine palladium dichloride was used to obtain a titanium oxide supported gold catalyst ("comparative catalyst(1)" hereinafter). Then, using comparative catalyst (1), the oxidation reaction of p-xylene was carried out under the same reaction conditions as those of Example 1. Thus, the comparative catalyst is made up of comparative catalyst (1), which does not contain a Group VIII element, and bismuth acetate oxide, and potassium acetate.

After the reaction was finished, the composition of the reaction mixture from which the comparative catalyst (1) has been removed was analyzed by gas chromatography and liquid chromatography, which revealed that the reaction mixture did not contain p-acetoxymethyl benzoic acid. The raw material, p-xylene, was recovered almost entirely from the reaction liquid.

EXAMPLE 5

To a 100 ml autoclave were added 5 g of acetoxymethyl benzoic acid, as the (acyloxyalkyl)aromatic carboxylic acids, which was obtained by the same reaction and operation as those of Example 1, 20 g of water, and 10 g of methanol, and the autoclave was sealed after adding 1.0 g of active carbon supported ruthenium as the reducing catalyst, in which ruthenium is supported on active carbon. The support amount (content) of ruthenium in the reducing catalyst was 5% by weight.

Thereafter, after replacing inside the autoclave by nitrogen gas, hydrogen gas was drawn into the autoclave and the pressure inside the autoclave was increased to $4.9 \times 10^6$ Pa (gauge pressure). Then, the autoclave was heated to 100° C. and a hydrogenation reaction was performed while stirring the reaction solution inside the autoclave until there was no further absorption of hydrogen.

After the reaction was finished, the resultant was cooled. The resultant was then filtered to separate the reducing catalyst, and the composition of the filtrate was analyzed by gas chromatography, which revealed that the conversion of p-acetoxymethyl benzoic acid was 100 mole % and that the filtrate contained 4.55 g (yield of 88 mole %; trans/cis mixture) of 4-acetoxymethyl cyclohexane carboxylic acid as a hydrogenated product of the p-acetoxymethyl benzoic acid.

The identification of the 4-acetoxymethyl cyclohexane carboxylic acid was made by the measurements of $^1$H-NMR and $^{13}$C-NMR. The spectral data of the compound are as follows.

$^1$H-NMR (solvent; $CDCl_3$); Chemical Shift Value δ (ppm): (multiplicity, equivalent proton number); δ: 0.8–2.8 (m, 9H); δ: 2.02 (s, 3H); δ: 2.57–2.62 (m, 1H); δ: 3.85 3.92 (m, 2H); δ: 10.6–11.4 (b, 1H).

$^{13}$C-NMR (solvent; $CDCl_3$); Chemical Shift Value δ (ppm): 20.8, 25.8, 27.6, 28.3, 35.2, 36.2, 41.0, 43.9, 68.0, 68.9, 171.1, 180.0, 180.6.

EXAMPLE 6

To a 50 ml round-bottomed flask equipped with a reflux condenser were added altogether 2 g of 4-acetoxymethyl cyclohexane carboxylic acid, as the (acyloxyalkyl)alicyclic carboxylic acids, which was obtained in Example 5, 6 g of water, and 26 mg of p-toluene sulfonic acid as an acid catalyst. Thereafter, the aqueous mixture in the flask was heated to 100° C., and a hydrolysis reaction was allowed for 3 hours with stirring.

After the reaction was finished, the aqueous solution was cooled. Then, the aqueous solution was filtered to separate the acid catalyst, and the composition of the aqueous solution was analyzed by liquid chromatography, which revealed that the conversion of the 4-acetoxymethyl cyclohexane carboxylic acid was 85 mole % and that the aqueous solution contained 1.34 g (yield of 84.8 mole %) of 4-hydroxymethyl cyclohexane carboxylic acid, which is the hydrolyzed product of 4 acetoxymethyl cyclohexane carboxylic acid, as the hydrohyalkyl alicyclic carboxylic acid in accordance with the present invention.

EXAMPLE 7

To a 100 ml round-bottomed flask equipped with a reflux condenser were added altogether 5 g of p-acetoxymethyl benzoic acid, as the (acyloxyalkyl)aromatic carboxylic acid, which was obtained by the same reaction and operation as those of Example 1, 10 g of water, and 1.85 g of sodium hydroxide as an alkali compound. Thereafter, the aqueous solution in the flask was heated to 100° C., and a hydrolysis reaction was allowed for 2 hour with stirring.

After the reaction was finished, the aqueous solution was cooled. Then, the aqueous solution was neutralized with 0.1 N of hydrochloric acid, and the composition of the aqueous solution was analyzed by liquid chromatography, which revealed that the conversion rate of the p-acetoxymethyl benzoic acid was 100 mole % and that the aqueous solution contained 3.91 g (yield of 100 mole %) of p-hydroxymethyl benzoic acid as the (hydroxyalkyl)aromatic carboxylic acids in accordance with the present invention.

EXAMPLE 8

To a three-necked round-bottomed flask equipped with a reflux condenser were added altogether 5 g of p-acetoxymethyl benzoic acid, as the (acyloxyalkyl) aromatic carboxylic acids, which was obtained by the same reaction and operation as those of Example 1, 50 ml of water, and 1.0 g of acidic ion exchange resin (Product Name: "Amberlist-15" provided by Japan Organo Co., Ltd.) as an acid catalyst. Thereafter, the aqueous mixture in the flask was heated to 100° C., and a hydrolysis reaction was allowed for an hour with stirring.

After the reaction was finished, the aqueous mixture was cooled. Then, the aqueous mixture was filtered to separate the acid catalyst, and the composition of the filtrate was analyzed by liquid chromatography, which revealed that the filtrate contained 3.2 g (yield of 82 mole %) of p-acetoxymethyl benzoic acid, which is the hydrolyzed product of p-acetoxymethyl benzoic acid, as the (hydroxyalkyl) aromatic carboxylic acids in accordance with the present invention.

EXAMPLE 9

To a 50 ml autoclave were added 3 g of p-hydroxymethyl benzoic acid, as the (hydroxyalkyl) aromatic carboxylic acids, which was obtained in Example 8, 12 g of water, and 6 g of methanol, and the autoclave was sealed after adding the reducing catalyst, 0.6 g of active carbon supported ruthenium, in which ruthenium is supported on active carbon. The support amount (content) of ruthenium in the reducing catalyst was 5% by weight.

Then, after replacing inside the autoclave with nitrogen gas, hydrogen gas was drawn into the autoclave to increase the pressure therein to $4.9 \times 10^6$ Pa (gauge pressure). Thereafter, the autoclave was heated to 100° C., and a hydrogenation reaction was performed while stirring the reaction liquid in the autoclave until there was no further absorption of hydrogen.

After the reaction was finished, the reaction mixture was cooled. Thereafter, the reaction mixture was filtered to separate the reducing catalyst, and the composition of the filtrate was analyzed by gas chromatography, which revealed that the conversion rate of the p-hydroxymethyl benzoic acid was 100 mole % and that the reaction liquid contained 2.71 g (yield of 87 mole %) of 4-hydroxymethyl cyclohexane carboxylic acid, which is the reduced product of the p-hydroxymethyl benzoic acid, as the (hydroxyalkyl) alicyclic carboxylic acids in accordance with the present invention.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

What is claimed is:

1. A method for producing (hydroxyalkyl) alicyclic carboxylic acids, comprising the steps of:

(i) producing (acyloxyalkyl) alicyclic carboxylic acids by hydrogenation of an aromatic ring of (acyloxyalkyl) aromatic carboxylic acids; and (ii) subjecting the (acyloxyalkyl) alicyclic carboxylic acids obtained in said step (i) to hydrolysis wherein the (acyloxyalkyl) alicyclic carboxylic acids have a structure represented by the following Formula (2)

$$R^6COO\text{—}CR^1R^2\text{—}Z\text{—}COOH \quad (2)$$

where Z is an alicyclic compound group of two or greater valency having six or more carbon atoms, $R^1$ is a hydrogen atom or alkyl group having a carbon number of 1 to 3, $R^2$ is a hydrogen atom, or alkyl group having a carbon number of 1 to 3, or —$OCOR^1$ group, $R^5$ is an alkyl group having a carbon number of 1 to 4, and $R^6$ is an alkyl group having a carbon number of 1 to 6, alkenyl group having a carbon number of 1 to 6, alkynyl group having a carbon number of 1 to 6, or a benzene ring, which may or may not include a substituent, wherein the (acyloxyalkyl) aromatic carboxylic acids have the following Formula (3)

$$R^6COO\text{—}CR^1R^2\text{—}Ar\text{—}COOH \quad (3)$$

where Ar is an aromatic ring of two or greater valency, $R^1$ is a hydrogen atom or alkyl group having a carbon number of 1 to 3, $R^2$ is a hydrogen atom, alkyl group having a carbon number of 1 to 3, or —$OCOR^5$ group, $R^5$ is an alkyl group having a carbon number of 1 to 4, and $R^6$ is an alkyl group having a carbon number of 1 to 6, alkenyl group having a carbon number of 1 to 6, alkynyl group having a carbon number of 1 to 6, or a benzene ring, which may or may not include a substituent, and wherein the (hydroxyalkyl) alicyclic carboxylic acids have a structure represented by the following Formula (5)

$$HO\text{—}CR^1R^2\text{—}Z\text{—}COOH \quad (5)$$

where Z is an alicyclic compound group of two or greater valency having six or more carbon atoms, $R^1$ is a hydrogen atom or alkyl group having a carbon number of 1 to 3, $R^2$ is a hydrogen atom, alkyl group having a carbon number of 1 to 3, or —$OCOR^5$ group, and $R^5$ is an alkyl group having carbon number of 1 to 4.

2. The method as set forth in claim 1, further comprising, before subjecting the aromatic ring of the (acyloxyalkyl) aromatic carboxylic acids to hydrogenation, the step of producing the (acyloxyalkyl)aromatic carboxylic acids by an oxidative esterification reaction of alkyl substituted aromatic compounds which are represented by the following Formula (1)

$$CHR^1R^2\text{—}Ar\text{—}(R^3)_n \quad (1)$$

where Ar is an aromatic ring of two or greater valency, $R^1$ is a hydrogen atom or alkyl group having a carbon number of 1 to 3, $R^2$ is a hydrogen atom, alkyl group having a carbon number of 1 to 3, or —$OCOR^5$ group, $R^3$ is an alkyl group having a carbon number of 1 to 4, —COOH group, —CHO group, —$CH_2R^4$ group, or —$COOR^5$ group, n is an integer of 1 to 5, $R^4$ is a halogen atom, —OH group, or —$OCOR^5$ group, and $R^5$ is an alkyl group having a carbon number of 1 to 4), and carboxylic acids in the presence of oxygen using a catalyst including an element which belongs to Group VIII of the periodic table.

3. A method for producing (acyloxyalkyl)alicyclic carboxylic acids, comprising the step of subjecting an aromatic ring of (acyloxyalkyl)aromatic carboxylic acids to hydrogenation wherein the (acyloxyalkyl) alicyclic carboxylic acid is represented by the following formula:

$$R^5COO\text{—}CR^1R^2\text{—}Z\text{—}COOH \quad (2)$$

where Z is an alicyclic compound group of two or greater valency, $R^1$ is a hydrogen atom or an alkyl group having a carbon number of 1 to 3, $R^2$ is a hydrogen atom, an alkyl group having a carbon number of 1 to 3, or an —$OCOR^5$ group, R5 is an alkyl group having a carbon number of 1 to 4, and $R^6$ is an alkyl group having a carbon number of 1 to 6, an alkenyl group having a carbon number of 1 to 6, an alkynyl group having a carbon number of 1 to 6, or a benzene ring, which may or may not include a substituent, and wherein the (acyloxyalkyl) aromatic carboxylic acids have the following Formula (3)

$$R^5COO\text{—}CR^1R^2\text{—}Ar\text{—}COOH \quad (3)$$

where Ar is an aromatic ring of two or greater valency, $R^1$ is a hydrogen atom or alkyl group having a carbon number of 1 to 3, $R^2$ is a hydrogen atom, alkyl group having a carbon number of 1 to 3, or —$OCOR^5$ group, $R^5$ is an alkyl group having a carbon number of 1 to 4, and $R^6$ is an alkyl group having a carbon number of 1 to 6, alkenyl group having a carbon number of 1 to 6, alkynyl group having a carbon number of 1 to 6, or a benzene ring, which may or may not include a substituent.

4. The method as set forth in claim 3, further comprising, before subjecting the aromatic ring of the (acyloxyalkyl) aromatic carbokylic acids to hydrogenation, the step of producing the (acyloxyalkyl) aromatic carboxylic acids by an oxidative esterification reaction of alkyl substituted aromatic compounds which are represented by the following Formula (1)

$$CHR^1R^2\text{—}Ar\text{—}(R^3) \quad (1)$$

where Ar is an aromatic ring of two or greater valency, $R^1$ is a hydrogen atom or alkyl group having a carbon number of 1 to 3, $R^2$ is a hydrogen atom, alkyl group having a carbon number of 1 to 3, or —$OCOR^6$ group, $R^3$ is an alkyl group having a carbon number of 1 to 4, —COOH group, —CHO group, —$CH_2R^4$ group, or —$COOR^5$ group, n is an integer of 1 to 5, $R^4$ is a halogen atom, —OH group, or —$OCOR^5$ group, and $R^5$ is an alkyl group having a carbon number of 1 to 4, and carboxylic acids in the presence of oxygen using a catalyst including an element which belongs to Group VIII of the periodic table.

5. (Acyloxyalkyl)alicyclic carboxylic acids which are represented by the following Formula (2)

$$R^6COO\text{—}CR^1R^2\text{—}Z\text{—}COOH \qquad (2)$$

where Z is an alicyclic compound group of two or greater valency, $R^1$ is a hydrogen atom or alkyl group having a carbon number of 1 to 3, $R^2$ is a hydrogen atom, alkyl group having a carbon number of 1 to 3, or —$OCOR^5$ group, $R^5$ is an alkyl group having a carbon number of 1 to 4, and $R^6$ is an alkyl group having a carbon number of 1 to 6, alkenyl group having a carbon number of 1 to 6, alkynyl group having a carbon number of 1 to 6, or a benzene ring, which may or may not include a substituent.

6. A method for producing (hydroxyalkyl)alicyclic carboxylic acids, comprising the steps of:
   (i) producing (hydroxyalkyl)aromatic carboxylic acids by hydrolysis of (acyloxyalkyl)aromatic carboxylic acids; and
   (ii) subjecting an aromatic ring of the (hydroxyalkyl) aromatic carboxylic acids obtained in said step (i) to hydrogenation.

7. The method as set forth in claim 6, further comprising, before subjecting the (acyloxyalkyl)aromatic carboxylic acids to hydrolysis, the step of producing the (acyloxyalkyl) aromatic carboxylic acids by an oxidative esterification reaction of alkyl substituted aromatic compounds which are represented by the following Formula (1)

$$CHR^1R^2\text{—}Ar\text{—}(R^3)_n \qquad (1)$$

where Ar is an aromatic ring of two or greater valency, $R^1$ is a hydrogen atom or alkyl group having a carbon number of 1 to 3, $R^2$ is a hydrogen atom, alkyl group having a carbon number of 1 to 3, or —$OCOR^6$ group, $R^3$ is an alkyl group having a carbon number of 1 to 4, —COOH group, —CHO group, —$CH_2R^4$ group, or —$COOR^5$ group, n is an integer of 1 to 5, $R^4$ is a halogen atom, —OH group, or —$OCOR^5$ group, and $R^5$ is an alkyl group having a carbon number of 1 to 4, and carboxylic acids in the presence of oxygen using a catalyst including an element which belongs to Group VII of the periodic table wherein the (acyloxyalkyl) aromatic carboxylic acid is represented by the following formula:

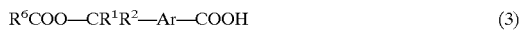
$$R^6COO\text{—}CR^1R^2\text{—}Ar\text{—}COOH \qquad (3)$$

where Ar is an aromatic ring of two or greater valency, $R^1$ is a hydrogen atom or an alkyl group having a carbon number of 1 to 3, $R^2$ is a hydrogen atom, an alkyl group having a carbon number of 1 to 3, or an —$OCOR^5$ group, $R^5$ is an alkyl group having a carbon number of 1 to 4, and $R^6$ is an alkyl group having a carbon number of 1 to 6, an alkenyl group having a carbon number of 1 to 6, an alkynyl group having a carbon number of 1 to 6, or a benzene ring, which may or may not say include a substituent.

8. A method for producing (hydroxyalkyl) alicyclic carboxylic acids, comprising the step of subjecting an aromatic ring of (hydroxyalkyl) aromatic carboxylic acids to hydrogenation using a catalyst which includes at least one element which is selected from the group consisting of rhodium and ruthenium.

9. A method for producing (hydroxyalkyl)aromatic carboxylic acids, comprising the step of subjecting (acyloxyalkyl)aromatic carboxylic acids to hydrolysis.

10. The method as set forth in claim 9, further comprising, before subjecting the aromatic ring of the (acyloxyalkyl) aromatic carboxylic acids to hydrolysis, the step of producing the (acyloxyalkyl)aromatic carboxylic acids by an oxidative esterification reaction of alkyl substituted aromatic compounds which are represented by the following Formula (1)

$$CHR^1R^2\text{—}Ar\text{—}(R^3)_n \qquad (1)$$

where Ar is an aromatic ring of two or greater valency, $R^1$ is a hydrogen atom or alkyl group having a carbon number of 1 to 3, $^2$ is a hydrogen atom, alkyl group having a carbon number of 1 to 3, or —$OCOR^5$ group, $R^3$ is an alkyl group having a carbon number of 1 to 4, —COOH group,—HO group,—$H_2R^4$ group, or —$COOR^5$ group, n is an integer of 1 to 5, $R^4$ is a halogen atom, —OH group, or —$OCOR^5$ group, and $R^5$ is an alkyl group having a carbon number of 1 to 4, and carboxylic acids in the presence of oxygen using a catalyst including an element which belongs to Group VIII of the periodic table wherein the (acyloxyalkyl) aromatic carboxylic acid is represented by the following formula:

$$R^5COO\text{—}CR^1R^2\text{—}Ar\text{—}COOH \qquad (3)$$

where Ar is an aromatic ring of two or greater valency, $R^1$ is a hydrogen atom or an alkyl group having a carbon number of 1 to 3, $R^2$ is a hydrogen atom, an alkyl group having a carbon number of 1 to 3, or an —$OCOR^5$ group, $R^5$ is an alkyl group having a carbon number of 1 to 4, and $R^6$ is an alkyl group having a carbon number of 1 to 6, an alkenyl group having a carbon number of 1 to 6, an alkynyl group having a carbon number of 1 to 6, or a benzene ring, which may or may not include a substituent.

11. A method for producing (acyloxyalkyl)aromatic carboxylic acids, comprising the step of performing an oxidative esterification reaction on alkyl substituted aromatic compounds which are represented by the following Formula (1)

$$CHR^1R^2\text{—}Ar\text{—}(R^3)_n \qquad (1)$$

where Ar is an aromatic ring of two or greater valency, $R^1$ is a hydrogen atom or alkyl group having a carbon number of 1 to 3, $R^2$ is a hydrogen atom, alkyl group having a carbon number of 1 to 3, or —$OCOR^5$ group, $R^3$ is an alkyl group having a carbon number of 1 to 4, —COOH group, —CHO group, —$CH_2R^4$ group, or —$COOR^5$ group, n is an integer of 1 to 5, $R^4$ is a halogen atom, —OH group, or —$OCOR^5$ group, and $R^5$ is an alkyl group having a carbon number of 1 to 4, and carboxylic acids in the presence of oxygen using a catalyst including an element which belongs to Group VIII of the periodic table wherein the (acyloxyalkyl) aromatic carboxylic acid is represented by the formula:

$$R^6COO\text{—}CR^1R^2\text{—}Ar\text{—}COOH \qquad (3)$$

where Ar is an aromatic ring of two or greater valency, $R^1$ is a hydrogen atom or an alkyl group having a carbon number of 1 to 3, $R^2$ is a hydrogen atom, an alkyl group having a carbon number of 1 to 3, or an —OCOR$^5$ group, R$^5$ is an alkyl group having a carbon number of 1 to 4, and R$^6$ is an alkyl group having a carbon number of 1 to 6, an alkenyl group having a carbon number of 1 to 6, an alkynyl group having a carbon number of 1 to 6, or a benzene ring, which may or may not include a substituent.

12. The method as set forth in claim 11, wherein the catalyst further includes at least one element which is selected from the group consisting of Group IB, Group IIB, Group IIIB, Group IVB, Group VB, Group VIB, and Group VIIA of the periodic table.

13. The method as set forth in claim 11, wherein the element is immobilized on a support.

14. The method as set forth in claim 1, wherein a catalyst containing either ruthenium or rhodium is used as a reduction catalyst in step (i).

15. The method as set forth in claim 2, wherein a catalyst used in the oxidative esterification reaction contains one or more of the elements nickel, palladium, platinum, and rhodium.

16. The method as set forth in claim 3, wherein a catalyst containing either ruthenium or rhodium is used as a reduction catalyst in the hydrogenation.

17. The method as set forth in claim 4, wherein a catalyst used in the oxidative esterification reaction contains one or more of the elements nickel, palladium, platinum, and rhodium.

18. The method as set forth in claim 7, wherein a catalyst used in the oxidative esterification reaction contains one or more of the elements nickel, palladium, platinum, and rhodium.

19. The method as set forth in claim 10, wherein a catalyst used in the oxidative esterification reaction contains one or more of the elements nickel, palladium, platinum, and rhodium.

20. The method as set forth in claim 11, wherein a catalyst used in the oxidative esterification reaction contains one or more of the elements nickel, palladium, platinum, and rhodium.

* * * * *

UNITED STATES PATENT AND TRADEMARK OFFICE
CERTIFICATE OF CORRECTION

PATENT NO.    : 6,444,843 B1
DATED         : September 3, 2002
INVENTOR(S)   : Yuuichi Satoh et al.

It is certified that error appears in the above-identified patent and that said Letters Patent is hereby corrected as shown below:

Title page,
Item [56], References Cited, U.S. PATENT DOCUMENTS
add:
       -- 4,130,719    12/1978    Cerefice et al.
          4,448,987     5/1984    Lillwitz -- add:
      -- FOREIGN PATENT DOCUMENTS
     BE 675 582 A  5/1966    Belgium
     09059188       3/1997    Japan
     101334/1975   8/1975    Japan
     96541/1973    12/1973   Japan
     1447136        1966      France
     2642496A1    3/1978    Germany --

OTHER PUBLICATIONS add:
-- Gordon D. Brindell, et al., "Polymer Applications of Some Terephthalaldehyde Derivatives", Ind. Eng. Chem., Prod. Res. Dev. Vol. 15, No. 1, 1976, pps. 83-88.
Okada, T., et al., "the Liquid-phase Oxidation of Methylbenzenes by the Cobalt-Copper-Bromide System," Bull. Chem. Soc. Jpn., 54, 2727 (1981) Vol. 54, No. 9, pps. 2724-2727.
Ader, U., et al., "Enzymatic Ester Hydrolysis and Synthesis, Two Approaches to Cycloalkane Derivatives of High Enantiomeric Purity," Tetr. Ltrs., Vol. 30, No. 14, pps. 1793-1796, 1989 Pergamon Press. --

Item [57], ABSTRACT,
Line 8, change "–COOR" to -- $-COOR^5$ --.

Column 29,
Line 26, change "$-OCOR^1$" to -- $-OCOR^5$ --.

Column 30,
Line 45, change "The" to -- A --;
Line 53, change "$CHR^1R^2-Ar-(R^3)$" to -- $CHR^1R^2-Ar-(R^3)_n$ --; and
Line 58, change "$-OCOR^6$" to -- $-OCOR^5$ --.

UNITED STATES PATENT AND TRADEMARK OFFICE
CERTIFICATE OF CORRECTION

PATENT NO. : 6,444,843 B1
DATED : September 3, 2002
INVENTOR(S) : Yuuichi Satoh et al.

It is certified that error appears in the above-identified patent and that said Letters Patent is hereby corrected as shown below:

Column 31,
Line 34, change "–$OCR^6$" to -- –$OCOR^5$ --; and
Line 58, delete "say".

Column 32,
Line 13, change -- $^2$ -- to -- $R^2$ --;
Line 16, change "–HO" to -- –CHO --; and
Line 16, change "–$H_2R^4$" to -- –$CH_2R^4$ --.

Signed and Sealed this

Fifteenth Day of April, 2003

JAMES E. ROGAN
*Director of the United States Patent and Trademark Office*